US008268549B2

(12) United States Patent
Ahmed et al.

(10) Patent No.: US 8,268,549 B2
(45) Date of Patent: *Sep. 18, 2012

(54) METHOD AND ASSAY FOR DETERMINING METHYLATION OF GAL3 PROMOTER FOR EARLY DIAGNOSIS OF PROSTATE CANCER

(75) Inventors: Hafiz Ahmed, Aldie, VA (US); Gerardo Raul Vasta, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 299 days.

This patent is subject to a terminal disclaimer.

(21) Appl. No.: 12/419,924

(22) Filed: Apr. 7, 2009

(65) Prior Publication Data

US 2009/0215066 A1  Aug. 27, 2009

Related U.S. Application Data

(63) Continuation-in-part of application No. 11/405,238, filed on Apr. 17, 2006, now Pat. No. 7,632,634.

(60) Provisional application No. 60/672,171, filed on Apr. 15, 2005.

(51) Int. Cl.
C12Q 1/68 (2006.01)
(52) U.S. Cl. .......................................................... 435/6
(58) Field of Classification Search .................. None
See application file for complete search history.

(56) References Cited

U.S. PATENT DOCUMENTS

| 7,252,935 | B2 | 8/2007 | Sidransky | |
| 7,632,634 | B2 * | 12/2009 | Ahmed et al. | 435/4 |
| 2006/0246496 | A1 | 11/2006 | Ahmed et al. | |

OTHER PUBLICATIONS

Ahmed et al (Tansitional oncology, 2009, 2:146-156).*
Jeronimo et al (Urology, 2002, 60:1131-1135).*
Chiariotti et al Biochimie vol. 81 p. 381 (1999) (IDS).*
Cairns et al (Clinical Cancer Research, 2001).*
Ruebel et al (Cancer Research, Feb. 2005, 65:1136-1140).*
Ahmed, Hafiz, et al., "Human Splenic galaptin: carbohydrate binding specificity and characterization of the combining site", "Biochemistry", 1990, pp. 5315-5319, vol. 29, No. 22.
Ahmed, Hafiz, et al., "Lymphoblastoid cell adhesion mediated by a dimeric and polymeric endogenous beta-galactoside-binding lectin (Galaptin)", "Journal of Molecular Recognition ", 1992, pp. 18, vol. 5.
Ahmed, Hafiz, et al., "Galectins: conservation of functionally and structurally relevant amino acid residues defines two types of . . . ", "Glycobiology", 1994, pp. 545-549, vol. 4, No. 5.
Ahmed, Hafiz, et al., "The primary structure and carbohydrate specificity of a beta-galactosyl-binding lectin from toad (Bufo arenarum . . . ", "The Journal of Biological Chemistry", 1996, pp. 33083-33094, vol. 271, No. 51.

Ahmed, Hafiz, et al., "Novel carbohydrate specificity of the 16-kDa galectin from Caenorhabditis elegans: binding to blood group precursor . . . ", "Glycobiology", 2002, pp. 451-461, vol. 12, No. 8.
Ahmed, Hafiz, et al., "Biochemical and molecular characterization of galectins from zebrafish (Danio rerio): notochord-specific expression . . . ", "Glycobiology", 2004, pp. 219-232, vol. 14, No. 3.
Ahmed, Hafiz, et al., "A novel solid phase assay for Lectin binding", "Ann. N.Y. Acad. Sci.", 1994, pp. 315-317, vol. 712.
Ahmed, Hafiz, et al., "Elasmobranch and Teleost Fish Contain Thiol-Dependent Beta-Galactoside-Binding Lectins That Are Cross-Reactive With . . . ", "Ann. N.Y. Acad. Sci.", 1994, pp. 318-320, vol. 712.
Ahmed, H. et al. , "Galectin-1 from Bovine Spleen: Biochemical Characterization, Carbohydrate Specificity and Tissue-Specific Isoform . . . ", Oct. 5, 1996, pp. 1007-1019, vol. 120.
Akahani, Shiro, et al., "Galectin-3: a novel antiapoptotic molecule with a functional BH1 (NWGR) domain of Bcl-2 family", "Cancer Research", Dec. 1, 1997, pp. 5272-5276, vol. 57.
Allen, H. et al., "Galaptin and Galaptin-Binding Glycoconjugates in Serum and Effusions of Carcinoma Patients ", "Tumor Biology ", 1993, pp. 360-368, vol. 14.
Avni, Orly, et al., "Complement receptor 3 of macrophages is associated with galectin-1-like protein", "J. Immunol.", 1998, pp. 6151-6158, vol. 160.
Barondes, Samuel H., et al., "Galectins. Structure and function of a large family of animal lectins", "The Journal of Biological Chemistry", Aug. 19, 1994, pp. 20807-20810, vol. 269, No. 33.
Benvenuto, Giovanna, et al., "Cell-specific transcriptional regulation and reactivation of galectin-1 gene expression are controlled by DNA . . . ", "Molecular and Cellular Biology", Jun. 1996, pp. 2736-2743, vol. 16, No. 6.
Bianchet, M. et al., "Soluble Beta-Galactosyl-Binding Lectin (Galectin) From Toad Ovary: Crystallographic Studies of Two Protein-Sugar Complex", "Proteins: Structure, Function, and Genetics", 2000, pp. 378-388, vol. 40.
Bidon, N. et al. , "Two messenger RNAs and five isoforms for Po66-CBP, a galectin-8 homolog in a human lung carcinoma cell line", "Gene", 2001, pp. 253-262, vol. 274.
Bidon-Wagner, N. et al., "Human Galectin-8 isoforms and cancer ", "Gycoconjugate Journal", 2004, pp. 557-563, vol. 19.
Califice, S. et al., "Dual activities galectin-3 in human prostate cancer: tumor suppression of nuclear galectin-3 versus tumor promotion . . . ", "Oncogene", Aug. 23, 2004, pp. 7527-7536, vol. 23, Publisher: Nature Publishing Group.
Camby, I. et al., "Galectins Are Differentially Expressed in Supratentorial Pilocytic Astrocytomas, Astrocytomas, Anaplastic Astrocytomas..", "Brain Pathology", 2001, pp. 12-26, vol. 11.
Caplan, Aaron, et al., "Prostate-specific antigen and the early diagnosis of prostate cancer", "Am. J. Clin. Pathol.", 2002, pp. S104-S108, vol. 117 (Suppl 1).
Chiariotti, Lorenzo, et al., "Control of galectin gene expression", "Biochimie", 1999, pp. 381-388, vol. 81.

(Continued)

Primary Examiner — Laura B Goddard
(74) Attorney, Agent, or Firm — Kelly K. Reynolds; Steven J. Hultquist; Hultquist PLLC

(57) ABSTRACT

A method and assay are described for determining prostate cancer and the general stage of progression of such cancer by quantifying levels of promoter methylation of gal-3, optionally in combination with the quantification of the level of GSTP1 promoter methylation, where the method and assay are non-invasive to a subject and can detect any of Stages I-IV prostate cancer.

10 Claims, 17 Drawing Sheets

OTHER PUBLICATIONS

Cho, Moonjae, et al., "Galectin-1, a beta-galactoside-binding lectin in Chinese hamster ovary cells", "The Journal of Biological Chemistry", Mar. 10, 1995, pp. 5207-5212, vol. 270, No. 10.

Colnot, Celine, et al., "The role of galectins in mouse development", "Trends in Glycoscience and Glycotechnology", Jan. 1997, pp. 31-40, vol. 9, No. 45.

Colnot, Celine, et al., "Uncoupling of Chondrocyte Death and Vascular Invasion in Mouse Galectin 3 Null Mutant Bones", "Developmental Biology ", Jan. 2001, pp. 203-214, vol. 229.

Cooper, Douglas N. W., et al., "Evidence for export of a muscle lectin from cytosol to extracellular matrix and for a novel secretory mechanism", "The Journal of Cell Biology", May 1, 1990, pp. 1681-1691, vol. 110.

Cooper, Douglas N. W., et al., "Endogenous muscle lectin inhibits myoblast adhesion to laminin", "The Journal of Cell Biology", Dec. 1, 1991, pp. 1437-1448, vol. 115, No. 5.

Cooper, D. , "Galectinomics: finding themes in complexity", "Biochimica et Biophysica Acta", 2002, pp. 209-231, vol. 1572.

Costa, M., et al., "Abstract Only: Galectin-3 gene expresssion is silenced by methylation of its promoter in murine melanoma cells", "Accessed Online at: http://web.archive.org/web/20050223095849/ http://direxlim.fm.usp.br/r24b.php", 2003.

Danguy, A. , "Immunohistochemical profile of galectin-8 expression in benign and malignant tumors of epithelial, mesenchymatous and . . . ", "Histology and Histopathology ", 2001, pp. 861-868, vol. 16.

Ellerhorst, Julie, et al., "Galectin-1 and galectin-3 expression in human prostate tissue and prostate cancer", "Urol. Res.", 1999, pp. 362-367, vol. 27.

Ellerhorst, Julie, et al., "Differential expression of endogenous galectin-1 and galectin-3 in human prostate cancer cell lines and effects of . . . ", "Int J Oncol.", 1999, pp. 217-224, vol. 14.

Fackler, Mary Jo, et al., "Quantitative multiplex methylation-specific PCR assay for the detection of promoter hypermethylation in multiple genes..", "Cancer Research", Jul. 1, 2004, pp. 4442-4452, vol. 64.

Frommer, Marianne, et al., "A genomic sequencing protocol that yields a positive display of 5-methylcytosine residues in individual DNA strands", "Proc. Natl. Acad. Sci. USA", Mar. 1992, pp. 1827-1831, vol. 89.

Gauthier, Laurent, et al., "Galectin-1 is a stromal cell ligand of the pre-B cell receptor (BCR) implicated in synapse formation between pre-B . . . ", "Proc. Natl. Acad. Sci. USA", Oct. 1, 2002, pp. 13014-13019, vol. 99, No. 20.

Gibson, Ursula E.M., et al., "A novel method for real time quantitative RT-PCR", "Genome Research", 1996, pp. 995-1001, vol. 6.

Glinsky, Vladislav V., et al., "Effects of Thomsen-Friedenreich antigen-specific peptide P-30 on beta-galactoside-mediated homotypic aggregation and . . . ", "Cancer Research", May 15, 2000, pp. 2584-2588, vol. 60.

Glinsky, Vladislav V., et al., "The role of Thomsen-Friedenreich antigen in adhesion of human breast and prostate cancer cells to the endothelium", "Cancer Research", Jun. 15, 2001, pp. 4851-4857, vol. 61.

Goletz, Steffen, et al., "Novel alphaGalNAc containing glycans on cytokeratins are recognized in vitro by galectins with type II carbohydrate . . . ", "Journal of Cell Science", 1997, pp. 1585-1596, vol. 110.

Gong, Hua Chang, et al., "The NH2 terminus of galectin-3 governs cellular compartmentalization and functions in cancer cells", "Cancer Research", Dec. 15, 1999, pp. 6239-6245, vol. 59.

Gotz, W. et al., "Detection and distribution of the carbohydrate binding protein galectin-3 in the human notochord, invertebral disc . . . ", "Differentiation", 1997, pp. 149-157, vol. 62.

Gu, Maojian, et al., "Selective modulation of the interaction of alpha7beta1 integrin with fibronectin and laminin by L-14 lectin during . . . ", "Journal of Cell Science", 1994, pp. 175-181, vol. 107.

Hadari, Yaron R., et al., "Galectin-8 binding to integrins inhibits cell adhesion and induces apoptosis", "Journal of Cell Science", 2000, pp. 2385-2397, vol. 113.

Hanahan, Douglas, et al., "The hallmarks of cancer", "Cell", Jan. 7, 2000, pp. 57-70, vol. 100.

Heid, Christian A., et al., "Real time quantitative PCR", "Genome Research", 1996, pp. 986-994, vol. 6.

Herman, James G., et al., "Methylation-specific PCR: a novel PCR assay for methylation status of CpG islands", "Proc. Natl. Acad. Sci.", Sep. 1, 1996, pp. 9821-9826, vol. 93, Published in: Washington, D.C., US.

Herman, James G., et al., "Gene silencing in cancer in association with promoter hypermethylation", "N. Engl. J. Med.", 2003, pp. 2042-2054, vol. 349.

Hernandez, Joseph D., et al., "Ah, sweet mystery of death! Galectins and control of cell fate", "Glycobiology", 2002, pp. 127R-136R, vol. 12, No. 10.

Hirabayashi, J. et al., "The family of metazoan metal-independent beta-galactoside binding lectins: structure, function, and molecular evolution", "Glycobiology", 1993, pp. 297-304, vol. 3, No. 4.

Inohara, Hidenori, et al., "Functional evidence that cell surface galectin-3 mediates homotypic cell adhesion", "Cancer Research", Aug. 1, 1995, pp. 3267-3271, vol. 55.

Iurisci, Ida, et al., "Concentrations of galectin-3 in the sera of normal controls and cancer patients", "Clinical Cancer Research", Apr. 2000, pp. 1389-1393, vol. 6.

Jain, S. et al. , "Improving the utility of prostate specific antigen (PSA) in the diagnosis of prostate cancer: the use of PSA derivatives", "Postgrad. Med. J.", 2002, pp. 646-650, vol. 78.

Jones, P. et al. , "The Fundamental Role of Epigenetic Events in Cancer", "Nature Reviews Genetics", Jun. 2002, pp. 415-428, vol. 3.

Kadrofske, M. et al., "The Human LGALS3 (Galectin-3) Gene: Determination of the Gene Structure and Functional Characterization of the Promoter", "Archives of Biochemistry and Biophysics", Jan. 1, 1998, pp. 7-20, vol. 349, No. 1.

Keetch, D. et al. , "Serial Protastic Biposies in Men With Persistently Elevated Serum Prostate SPpecific Antigen Values", "The Journal of Urology", Jun. 1994, pp. 1571-1574, vol. 151.

Kondoh, N. et al., "Activation of Galectin-1 gene in human hepatocellular carcinoma involves methylation-sensitive complex formations at . . . ", "Int J Oncol.", 2003, pp. 1575-1583, vol. 23.

Leffler, Hakon, et al., "Specificity of binding of three soluble rat lung lectins to substituted and unsubstituted mammalian beta-galactosides", "The Journal of Biological Chemistry", Aug. 5, 1986, pp. 10119-10126, vol. 261, No. 22.

Leffler, Hakon, et al., "Introduction to galectins", "Glycoconjugate Journal", 2004, pp. 433-440, vol. 19.

Levy, Yifat, et al., "Galectin-8 functions as a matricellular modulator of cell adhesion", "The Journal of Biological Chemistry", Aug. 17, 2001, pp. 31285-31295, vol. 276, No. 33.

Liao, Der-Ing, et al., "Structure of S-lectin, a developmentally regulated vertebrate beta-galactoside-binding protein", "Proc. Natl. Acad. Sci. USA", Feb. 1994, pp. 1428-1432, vol. 91.

Liu, F. , "Short Analytical Review: Galectins: A New Family of Regulators of Inflammation", "Clinical Immunology", Nov. 2000, pp. 79-88, vol. 97, No. 2.

Liu, F. et al., "Galectins As Modulators of Tumour Progression", "Nature Reviews: Cancer", Jan. 2005, pp. 29-41, vol. 5.

Matarrese, P. et al. , "Galectin-3 Overexpression Protects From Apoptosis by Improving Cell Adhesion Properties", "Int. J. Cancer", 2000, pp. 545-554, vol. 85.

Mizejewski, G., "Role of Integrins in Cancer: Survey of Expression Patterns", "Intergrins Expression in Cancer", 1999, pp. 124-138, Publisher: Society for the Experimental Biology and Medicine.

Nagia-Makker, P. et al. , "Carbohydrate-binding proteins in cancer, and their ligands as therapeutic agents.", "Trends in Molecular Medicine", Apr. 2, 2002, vol. 8, No. 4.

Nangia-Makker, Pratima, et al., "Galectin-3 induces endothelial cell morphogenesis and angiogenesis", "American Journal of Pathology", Mar. 2000, pp. 899-909, vol. 156, No. 3.

Ozeki, Y.et al., "Tissue fibronection is an endogenous ligand for galectin-1", "Glycobiology", 1995, pp. 255-261, vol. 5, No. 2.

Pacis, R. et al. , "Decreased Galectin-3 Expression in", "The Prostate", 2000, pp. 118-123, vol. 44.

Park, Jung W., et al., "Association of galectin-1 and galectin-3 with gemin4 in complexes containing the SMN protein", "Nucleic Acids Research", 2001, pp. 3595-3602, vol. 27, No. 17.

Paz, A. et al., "Galectin-1 binds oncogene H-Ras to mediate Ras membrane anchorage and cell transfomration", "Oncogene", Sep. 2001, pp. 7486-7493, vol. 20, Publisher: Nature Publishing Company.

Perillo, N. et al., "Apotosis of T-Cells Mediated by Galectin 1", "Letters to Nature", Dec. 14, 1995, pp. 736-739, vol. 378, Publisher: Nature.

Perillo, N. et al., "Galectins: Versatile modulators of cell adhesion, cell proliferation, and cell death", "J Mol. Med", 1998, pp. 402-412, vol. 76.

Puche, A. et al., "Role of Galectin-1 in the Developing Mouse olfactory system", "Developmental Biology", 1996, pp. 274-287, vol. 179, Publisher: Academic Press Inc.

Rabinovich, G. et al., "Role of galectins in inflammatory and immunomodulatory processes", "Biochimica et Biophysica Acta", 2002, pp. 274-284, vol. 1572.

Rabinovich, G. et al., "Shedding Light on the Immunomodulatory properties of galectins", "Glycoconjugate Journal", 2004, pp. 565-573, vol. 19.

Rosenberg, Ian, et al., "Mac-2-binding glycoproteins", "The Journal of Biological Chemistry", Oct. 5, 1991, pp. 18731-18736, vol. 266, No. 28.

Rubinstein, Natalia, et al., "Targeted inhibition of galectin-1 gene expression in tumor cells results in heightened T cell-mediated rejection: . . . ", "Cancer Cell", Mar. 2004, pp. 241-251, vol. 5.

Salvatore, P. et al., "High resolution methylation analysis of the galectin-1 gene promoter region in expressing and nonexpressing tissues", "FEBS Letters", 1998, pp. 152-158, vol. 421.

Schwarz, F. et al., "Thermodynamics of Bovine Spleen Galectin-1 Binding to Disaccharides: Correlation with Structure and its Effect on . . . ", "Biochemistry", 1998, pp. 5867-5877, vol. 37, No. 17.

Singal, Rakesh, et al., "Cytosine methylation represses glutathione S-transferase P1 (GSTP1) gene expression in human prostate cancer cells", "Cancer Research", Jun. 15, 2001, pp. 4820-4826, vol. 61.

Stewart, Delisha A., et al., "Changes in extracellular matrix (ECM) and ECM-associated proteins in the metastatic progression of prostate cancer", "Reprod. Biol. Endocrinol.", 2004, pp. 2-14, vol. 2.

Su, Zao-Zhong, et al., "Surface-epitope masking and expression cloning identifies the human prostate carcinoma tumor antigen gene PCTA-1 . . . ", "Proc. Natl. Acad. Sci. USA", Jul. 1996, pp. 7252-7257, vol. 93.

Symons, Antony, et al., "Characterization of the interaction between galectin-1 and lymphocyte glycoproteins CD45 and Thy-1", "Glycobiology", 2000, pp. 559-563, vol. 10, No. 6.

Thompson, Ian M., et al., "Prevalence of prostate cancer among men with a prostate-specific antigen level less than or equal to 4.0 ng per ML", "New Eng. J. Med.", May 27, 2004, pp. 2239-2246, vol. 350, No. 22.

Van Den Brule, S. et al., "Increased expression of galectin-1 in carcinoma associated stroma predicts poor outcome in prostate carcinoma patients", "J. Pathol.", 2001, pp. 80-87, vol. 193.

Van Den Brule, S. et al., "Expression of Galectins in Cancer: a critical review", "Glycoconjugate Journal", 2004, pp. 537-542, vol. 19.

Vasta, Gerardo R., et al., "Galectins from amphibian species: carbohydrate specificity, molecular structure and evolution", "Trends in Glycoscience and Glycotechnology", Jan. 1997, pp. 131-144, vol. 9, No. 45.

Vasta, G. et al., "C-type lectins and galectins mediate innate and adaptive immune functions: their roles in the complement activation . . . ", "Developmental and Comparative Immunology", 1999, pp. 401-420, vol. 23.

Vasta, Gerardo R., et al., "Galectins in telost fish: Zebrafish (*Danio rerio*) as a model species to address their biological riles in development . . . ", "Glycoconjugate Journal", Jan. 2004, pp. 503-521, vol. 21.

Vasta, G. et al., "Structural and functional diversity of lectin repertoires in invertebrates, protochordates and ectothermic vertebrates", "Current Opinion in Structural Biology", 2004, pp. 617-630, vol. 14.

Warfiled, P. et al., "Adhesion of Human Breast Carcinoma to Extracellular Matrix Proteins is Modulated by Galectin-3", "Invasion Metastasis", 1997, pp. 101-112, vol. 17.

Warnecke, Peter M., et al., "Cytosine methylation and human cancer", "Current Opinion in Oncology", 2000, pp. 68-73, vol. 12.

Yang, Ri-Yao, et al., "Expression of galectin-3 modulates T-cell growth and apoptosis", "Proc. Natl. Acad. Sci. USA", Jun. 1996, pp. 6737-6742, vol. 93.

Yang, Ri-Yao, et al., "Cell cycle regulation by galectin-12, a new member of the galectin superfamily", "The Journal of Biological Chemistry", Jun. 8, 2001, pp. 20252-20260, vol. 276, No. 23.

Yu, Fei, et al., "Galectin-3 translocates to the perinuclear membranes and inhibits cytochrome c release from the mitochondria", "The Journal of Biological Chemistry", May 3, 2002, pp. 15819-15827, vol. 277, No. 18.

Zhou, Q. et al., "L-14 Lectin Recognition of Laminin and Its Promotion of in Vitro Cell Adhesion", "Archives of Biochemistry and Biophysics", Jan. 1993, pp. 6-17, vol. 300, No. 1.

Zick, Y. et al., "Role of galectin-8 as a modulator of cell adhesion and cell growth", "Glycoconjugate Journal", 2004, pp. 517-526, vol. 19.

* cited by examiner gal8a/Po66-CBP/PCTA-1 gal8b/Po66-CBP-1S1 gal8c gal8d (proto)/Po66-CBP-1S2 gal8e (proto)/Po66-CBP-IS1-IS2 gal8f (proto)/Po66-CBP-IS1-IE-IS2

Newly discovered isoform:

gal8g (proto)

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: HuG3BPF3 primer

<400> SEQUENCE: 1
taaggtggaa gtggtaaggg g                                              21

<210> SEQ ID NO 2
<211> LENGTH: 21
<212> TYPE: DNA
<213> ORGANISM: Unknown
<220> FEATURE:
<223> OTHER INFORMATION: gal3 wild type fragment source for SEQ ID NO: 1
      primer

<400> SEQUENCE: 2
caaggtggaa gtggcaaggg g                                              21

<210> SEQ ID NO 3

```
<211> LENGTH: 20
<212> TYPE: DNA
<213> ORGANISM: Artificial Sequence
<220> FEATURE:
<223> OTHER INFORMATION: HuG3BPR3 primer

<400> SEQUENCE: 3
ccccacacaa ctcaccactc                                               20

<210> SEQ ID NO 4
<211> LENGTH: 20
<212> TYPE: DNA
<213> ORGANISM: Unknown
<220> FEATURE:
<223> OTHER INFORMATION: gal3 wild type fragment source for SEQ ID NO: 3
      primer

<400> SEQUENCE: 4
ccccgcgcag ctcaccgctc                                               20

<210> SEQ ID NO 5
<211> LENGTH: 15
<212> TYPE: DNA
<213> ORGANISM: Unknown
<220> FEATURE:
<223> OTHER INFORMATION: CpG-containing DNA fragment

<400> SEQUENCE: 5
gcgattaggc gtacg                                                    15

<210> SEQ ID NO 6
<211> LENGTH: 15
<212> TYPE: DNA
<213> ORGANISM: Unknown
<220> FEATURE:
<223> OTHER INFORMATION: unmethylated CpG-containing DNA fragment after
      bisulfite treatment

<400> SEQUENCE: 6
gugattaggu gtaug                                                    15

<210> SEQ ID NO 7
<211> LENGTH: 15
<212> TYPE: DNA
<213> ORGANISM: Artificial Sequence
<220> FEATURE:
<223> OTHER INFORMATION: U primer

<400> SEQUENCE: 7
cactaatcca catac                                                    15

<210> SEQ ID NO 8
<211> LENGTH: 15
<212> TYPE: DNA
<213> ORGANISM: Artificial Sequence
<220> FEATURE:
<223> OTHER INFORMATION: M primer

<400> SEQUENCE: 8
cgctaatccg catgc                                                    15

<210> SEQ ID NO 9
<211> LENGTH: 18
<212> TYPE: DNA
<213> ORGANISM: Artificial Sequence
<220> FEATURE:
<223> OTHER INFORMATION: HuG3BPF3 primer
```

```
<400> SEQUENCE: 9
ggagagggtg ggggatag                                                    18

<210> SEQ ID NO 10
<211> LENGTH: 18
<212> TYPE: DNA
<213> ORGANISM: Artificial Sequence
<220> FEATURE:
<223> OTHER INFORMATION: gal3 wild type fragment source for SEQ ID NO: 9
      primer

<400> SEQUENCE: 10
ggagagggcg ggggacag                                                    18

<210> SEQ ID NO 11
<211> LENGTH: 18
<212> TYPE: DNA
<213> ORGANISM: Artificial Sequence
<220> FEATURE:
<223> OTHER INFORMATION: G3BPR3 primer

<400> SEQUENCE: 11
acaccctctc ccctaccc                                                    18

<210> SEQ ID NO 12
<211> LENGTH: 17
<212> TYPE: DNA
<213> ORGANISM: Artificial Sequence
<220> FEATURE:
<223> OTHER INFORMATION: gal3 wild type fragment source for SEQ ID NO:
      11 primer

<400> SEQUENCE: 12
gcgccctctc cctgccc                                                     17

<210> SEQ ID NO 13
<211> LENGTH: 17
<212> TYPE: DNA
<213> ORGANISM: Artificial Sequence
<220> FEATURE:
<223> OTHER INFORMATION: HuG3BPMF1 primer

<400> SEQUENCE: 13
cgtttcgtcg gcgttcg                                                     17

<210> SEQ ID NO 14
<211> LENGTH: 18
<212> TYPE: DNA
<213> ORGANISM: Artificial Sequence
<220> FEATURE:
<223> OTHER INFORMATION: HuG3BPMR1 primer

<400> SEQUENCE: 14
cacgcaactc accgctcg                                                    18

<210> SEQ ID NO 15
<211> LENGTH: 28
<212> TYPE: DNA
<213> ORGANISM: Artificial Sequence
<220> FEATURE:
<223> OTHER INFORMATION: HuG3BPUF1 primer

<400> SEQUENCE: 15
gaggtttgga gttattgttt tgttggtg                                         28

<210> SEQ ID NO 16
```

```
<211> LENGTH: 21
<212> TYPE: DNA
<213> ORGANISM: Artificial Sequence
<220> FEATURE:
<223> OTHER INFORMATION: HuG3BPUR1 primer

<400> SEQUENCE: 16
ccccacacaa ctcaccactc a                                              21

<210> SEQ ID NO 17
<211> LENGTH: 24
<212> TYPE: DNA
<213> ORGANISM: Artificial Sequence
<220> FEATURE:
<223> OTHER INFORMATION: GSTP1UF1 primer

<400> SEQUENCE: 17
ggttagttgt gtggtgattt tggg                                           24

<210> SEQ ID NO 18
<211> LENGTH: 20
<212> TYPE: DNA
<213> ORGANISM: Artificial Sequence
<220> FEATURE:
<223> OTHER INFORMATION: GSTP1UR1 primer

<400> SEQUENCE: 18
aacctcacaa cctccaaacc                                                20

<210> SEQ ID NO 19
<211> LENGTH: 18
<212> TYPE: DNA
<213> ORGANISM: Artificial Sequence
<220> FEATURE:
<223> OTHER INFORMATION: GSTP1MF1 primer

<400> SEQUENCE: 19
tagttgcgcg gcgatttc                                                  18

<210> SEQ ID NO 20
<211> LENGTH: 18
<212> TYPE: DNA
<213> ORGANISM: Artificial Sequence
<220> FEATURE:
<223> OTHER INFORMATION: GSTP1MR1 primer

<400> SEQUENCE: 20
aaaacctcgc gacctccg                                                  18

<210> SEQ ID NO 21
<211> LENGTH: 18
<212> TYPE: DNA
<213> ORGANISM: Artificial Sequence
<220> FEATURE:
<223> OTHER INFORMATION: GSTP1MF1 primer

<400> SEQUENCE: 21
cggggtgtag cggtcgtc                                                  18

<210> SEQ ID NO 22
<211> LENGTH: 21
<212> TYPE: DNA
<213> ORGANISM: Artificial Sequence
<220> FEATURE:
<223> OTHER INFORMATION: GSTP1MR1 primer

<400> SEQUENCE: 22
```

```
gccccaatac taaatcacga c                                             21
```

<210> SEQ ID NO 23
<211> LENGTH: 25
<212> TYPE: DNA
<213> ORGANISM: Artificial Sequence
<220> FEATURE:
<223> OTHER INFORMATION: GSTP1UF2 primer

<400> SEQUENCE: 23

```
gatgtttggg gtgtagtggt tgttg                                         25
```

<210> SEQ ID NO 24
<211> LENGTH: 26
<212> TYPE: DNA
<213> ORGANISM: Artificial Sequence
<220> FEATURE:
<223> OTHER INFORMATION: GSTP1UR2 primer

<400> SEQUENCE: 24

```
ccaccccaat actaaatcac aacacc                                        26
```

<210> SEQ ID NO 25
<211> LENGTH: 40
<212> TYPE: DNA
<213> ORGANISM: Artificial Sequence
<220> FEATURE:
<223> OTHER INFORMATION: methylated gal3 promoter in LNCaP

<400> SEQUENCE: 25

```
ggcgtcgttt cgtttcggga gaggcgggtc gggcggggtt                         40
```

<210> SEQ ID NO 26
<211> LENGTH: 40
<212> TYPE: DNA
<213> ORGANISM: Artificial Sequence
<220> FEATURE:
<223> OTHER INFORMATION: complement to SEQ ID NO: 25

<400> SEQUENCE: 26

```
ccgcagcaaa gcaaagccct ctccgcccag cccgccccaa                         40
```

<210> SEQ ID NO 27
<211> LENGTH: 40
<212> TYPE: DNA
<213> ORGANISM: Artificial Sequence
<220> FEATURE:
<223> OTHER INFORMATION: bisulfite treated methylated gal3 promoter in
      LNCaP

<400> SEQUENCE: 27

```
ggtgttgttt tgttttggga gaggtgggtt gggtggggtt                         40
```

<210> SEQ ID NO 28
<211> LENGTH: 40
<212> TYPE: DNA
<213> ORGANISM: Artificial Sequence
<220> FEATURE:
<223> OTHER INFORMATION: complement to SEQ ID NO: 27

<400> SEQUENCE: 28

```
ccacaacaaa acaaaaccct ctccacccaa cccaccccaa                         40
```

METHOD AND ASSAY FOR DETERMINING METHYLATION OF GAL3 PROMOTER FOR EARLY DIAGNOSIS OF PROSTATE CANCER

CROSS-REFERENCE TO RELATED APPLICATIONS

The present application is a continuation in part of U.S. application Ser. No. 11/405,238, filed Apr. 17, 2006, published Nov. 2, 2006 as U.S. Publication No. 2006/0246496 and issued as U.S. Pat. No. 7,632,634, which claims priority under 35U.S.C. 517 119(e) to U.S. patent application Ser. No. 60/672,171 filed Apr. 15, 2005. The entire contents of the foregoing applications and publications are incorporated by reference herein in their entirety.

FIELD OF THE INVENTION

The present invention relates to detection of prostate cancer, and more particularly, to a non-invasive method for the accurate diagnosis of prostate cancer by determining and comparing galectin promoter methylation in a biological sample and, optionally, further determining and comparing promoter methylation of GSTP1 in the biological sample.

BACKGROUND OF THE INVENTION

Prostate cancer is the second most common cancer in men (after skin cancer), and the second leading cause of cancer death in men (after lung cancer). In the United States, there are greater than 300,000 newly diagnosed cases each year, and about 40,000 of patients die of the disease yearly (Stewart et al., 2004). Approximately 90% of patients with advanced prostate cancer develop osseous metastases. Once prostate cancer metastasizes to the bone it is difficult to eradicate, and typically, these patients have a mean survival time of nine months to one year (Stewart et al., 2004).

Approximately 30% of men over the age of 55 harbor latent prostate cancers, detectable only at postmortem examination. Greater than 95% of cancers of the prostate are gland-forming adenocarcinomas, which have a predilection for the peripheral zones. The remaining prostate cancers are divided between squamous cell and transitional cell carcinomas (arising from the prostatic ducts), small cell and other neuroendocrine tumors, and rarely, carcinosarcomas. The histologic precursor lesion of prostatic adenocarcinomas is prostatic intraepithelial neoplasia (PIN), which shares the cytological features of cancer as well as many of the associated genetic abnormalities. Unlike adenocarcinomas, PIN occurs within preexisting acinar structures, and is divided into low-grade (meaning slightly unusual) and high-grade (very unusual and close to being called cancer) variants. The latter is a more reproducible diagnosis and also has a stronger morphologic, genetic and clinical association with prostate cancer. In fact, the presence of isolated high-grade PIN in needle biopsy specimens strongly suggests that there is a co-existing carcinoma in the prostate.

Although a considerable proportion of prostate cancers grow slowly and are not considered to require urgent intervention, some grow quickly and are deadly. If these cancers are detected in early stages, such as Stages I and II, however, they can be effectively treated and cured. Combined with the digital rectal examination (DRE), the prostate specific antigen (PSA) test has been widely used to detect prostate cancer in its early stages. This test measures the serum levels of PSA, an enzyme that is produced by the prostate and released into the bloodstream to reach concentrations below 3-4 ng/ml in healthy individuals. PSA levels above that value are considered as an indication of possible prostate cancer. However, PSA is specific for prostate tissues, but not for prostate cancer. Multiple factors such as benign prostatic hyperplasia (BPH), prostatitis, prostatic ischemia or infarction, and even sexual activity can cause of elevated levels of PSA. Further, serum PSA levels are not a sensitive indicator for prostate cancer, as these may be normal despite the presence of the disease (Thompson et al., 2004).

Thus, the PSA screening method for early detection of prostate cancer is flawed by potential false positive and false negative results (sensitivity 90%; specificity 10-31%) (Thompson et al., 2004; Hessels et al., 2004; Keetch et al. 1994). False positives may lead to additional medical procedures that have potential risks, represent significant financial costs, and create anxiety for the patient and his family. Actually, only 25 to 30 percent of men who have a biopsy due to elevated PSA levels are diagnosed with prostate cancer (Keetch et al., 1994). Several modifications of the standard PSA test have been developed, and may be beneficial for select populations (Caplan and Kratz, 2002). However, uncertainty about the natural progression of prostate cancer and inherent limitations of PSA test raises serious concerns about the reliability and potential benefits of universal screening, and the recommendations of various organizations are conflictive (Caplan and Kratz, 2002).

Attempts to relate cancer-related PSA to PSA density using transrectal ultrasound or to relate PSA to velocity of change with time have been helpful but flawed (Jain et al., 2002). PSA forms complexes with various serum factors, including alpha 1-antichymotrypsin, and such complex formation is significantly higher in prostate carcinoma (PC) than in benign prostatic conditions; in general, the higher the proportion of free PSA, the lower the risk of cancer (Jain et al., 2002). Since there is a tendency to biopsy all individuals with PSA values above 3.5-4.0, using the "free" PSA to total PSA ratio could reduce negative prostate biopsies by 21-35%. Therefore, the test may be helpful in deciding whether a biopsy should be done. However, PSA cannot be used as a prognostic marker.

A variety of prognostic markers have come recently into vogue as prognostic indicators in prostate cancers. For example, DNA aneuploidy in prostate cancers correlates with a higher stage disease and shortened survival. The role of MIB-1 labeling index as a measure of proliferation, bcl-2 expression, loss of E-cadherin expression, and abnormal p53 accumulation have been proposed as prognostic indicators. Recently, additional assays have been established, based on the detection of the specific serum marker EPCA-2 (sensitivity 94%, specificity 92%) (Leman et al., 2007), and non-invasive detection methods of prostate cancer in body fluids such as urine and ejaculates based on over expression of telomerase (sensitivity 58%, specificity 100%) or the DD3 (PCA3) gene (sensitivity 67%, specificity 83%) (Hessels et al., 2004), and hyper-methylation of a four-gene cohort including glutathione S-transferase P1 (GSTP1) (theoretical sensitivity 73%, theoretical specificity 98%) (Hoque et al., 2005).

Epigenetic alterations, including hypermethylation of gene promoters, are also early events in neoplastic progression (Hanahan et al., 2000). Such alterations are believed to contribute to the neoplastic process by transcriptional silencing of tumor suppressor gene expression (Jones et al., 2002). Thus, methylated genes can serve as biomarkers for early detection of cancer (Fackler et al. 2004). In past years, several qualitative and quantitative PCR methods based on methylation of single genes (such as glutathione S-transferase P1

(GSTP1), specificity 79%; Cairns et al., 2001) or multiple-gene cohort (such as P16/ARF/MGMT/GSTP1, theoretical sensitivity 73%, theoretical specificity 98%; Hoque et al., 2005) and, recently, a multiplexed urine assay consisting of 3 methylation markers, GSTP1, RARB, and APC (sensitivity 55%, specificity 80%) has been developed (Vener et al., 2008). However, these detection methods are yet to be improved in both sensitivity and specificity, and most importantly, they are unsuitable for the detection of early stages of prostate cancer (Vener et al., 2008; Tokumaru et al., 2004).

However, the search to identify "ideal" marker(s) that would foretell disease progression and aggressiveness in newly diagnosed prostate cancers is ongoing. Cell surface proteins that modulate cell-cell and cell-extracellular matrix interactions are currently subjects of intense research in cancer biology. In particular, galectins, a family of beta-galactoside binding lectins, have been proposed to mediate diverse biological processes such as embryogenesis (Ahmed et al., 2004), inflammation (Rabinovich et al., 2002), apoptosis (Liu et al., 2000), and tumor metastasis (van den Brule et al., 2004).

Therefore, markers that would rigorously diagnose the presence of the disease in the early stages and serve as an indicator of disease progression and aggressiveness in prostate cancer have yet to be identified.

SUMMARY OF THE INVENTION

The present invention relates to methods for determining prostate cancer and determining the general stage of progression of such cancer by quantifying levels of promoter methylation of different galectin isoforms in a biological sample and, optionally, further determining and comparing promoter methylation of GSTP1 in the biological sample.

In another aspect the invention provides a method for determining prostate cancer in a subject, the method comprising
  obtaining a biological sample from the subject;
  determining the level of gal3 promoter methylation; and
  comparing the level of gal3 promoter methylation in the sample relative to the level of gal3 promoter methylation found in a normal biological sample of the same type, wherein an increase in the level of gal3 promoter methylation is indicative of prostate cancer in the subject and the relative level of increased methylation in the sample is indicative of the stage of the cancer.

In still another aspect the invention provides a method for determining prostate cancer in a subject, the method comprising:
  obtaining a biological sample from the subject;
  determining the level of gal3 promoter methylation;
  determining the level of GSTP1 promoter methylation;
  comparing the level of gal3 promoter methylation in the sample relative to the level of gal3 promoter methylation found in a normal biological sample of the same type; and
  comparing the level of GSTP1 promoter methylation in the sample relative to the level of GSTP1 promoter methylation found in a normal biological sample of the same type;
  wherein an increase in the level of gal3 promoter methylation or GSTP1 promoter methylation is indicative of prostate cancer in the subject and the relative level of increased methylation in the sample is indicative of the stage of the cancer.

In a further aspect the invention provides an assay for determining prostate cancer in a subject, the assay comprising:
  isolating a single-stranded DNA encoding gal3 from a biological sample taken from the subject;
  treating the single-stranded DNA with bisulfite to convert non-methylated cytosine into uracil; and
  determining the level of methylation of the gal3 promoter region of the single stranded DNA, wherein an increase of gal3 promoter methylation is an indication of prostate cancer in the subject.

DETAILED DESCRIPTION OF THE INVENTION

Figure 1:
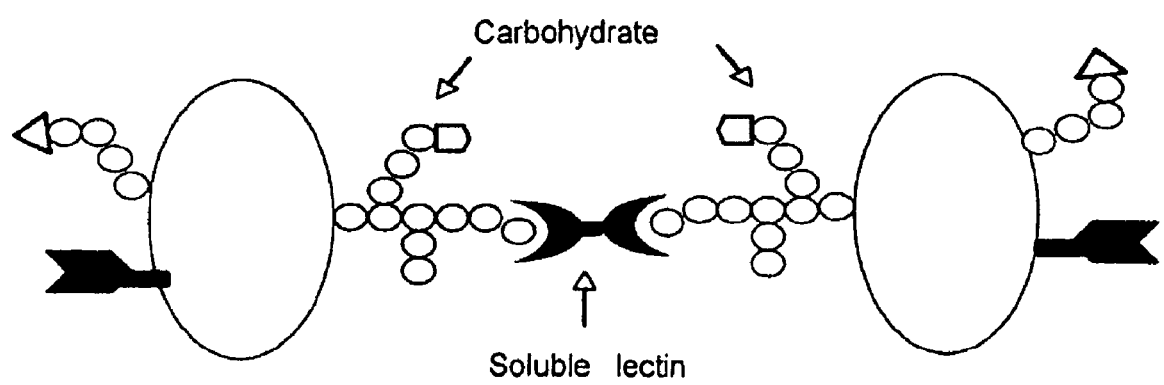
FIG. 1 is a schematic representation of lectin-carbohydrate-mediated cell-cell interaction. Lectins can be soluble or membrane-bound.

There is growing evidence that complex carbohydrate structures encode information that modulates interactions between cells, or cell and the extracellular matrix (ECM), by specifically binding to carbohydrate-binding proteins, such as galectins (Liu and Rabinovich, 2005; Rabinovich et al., 2004; Rubinstein et al., 2004) as shown in FIG. 1.

Figure 2:
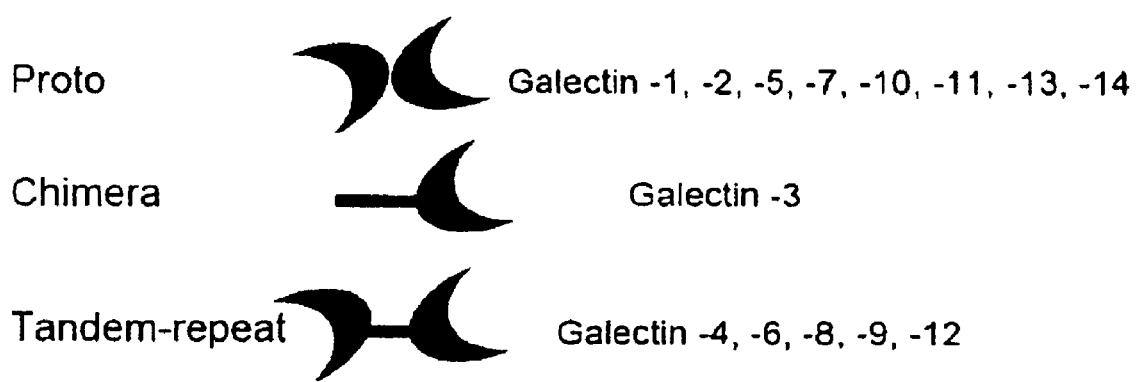
FIG. 2 shows the classification of galectins: Schematic representation of proto-, chimera, and tandem-repeat type galectins. Multiple galectin members are known for proto- and tandem-repeat type. They are numbered according to the order of their discovery (Barondes et al., 1994; Leffler et al., 2004).

Galectins, an evolutionarily conserved family of β-galactoside-binding proteins (previously known as S-type lectins), have been identified in most animal taxa and fungi (Cooper, 2002; Leffer et al., 2004). They are present not only in the cytosol but also in the ECM (Cooper and Barondes, 1990; Cho and Cummings, 1995). Based on structural features, galectins have been classified in three types: "proto," "chimera," and "tandem-repeat" as shown in FIG. 2 (Hirabayashi and Kasai, 1993). Proto type galectins contain one "carbohydrate recognition domain" (CRD) per subunit, and usually form homodimers of non-covalently-linked subunits. Galectins 1, 2, 5, 7, 10, 11, 13, 14 and 15 have been identified as proto type galectins. The chimera type galectins have a C-terminal domain similar to the proto type, but exhibit an N-terminal domain that is responsible for interactions between subunits, and other CRD-independent functions. The one CRD is connected to a collagen-like sequence rich in proline and glycine (Gong 1999). Galectin 3 has been identified as a chimera type galectin. Tandem-repeat galectins, in which two CRDs are joined by a linker peptide, are monomeric. Galectins 4, 6, 8, 9, and 12 have been identified as tandem-repeat type galectins. The dimerization of proto type galectins is critical for their function in mediating cell-cell or cell-ECM interactions (Barondes et al., 1994), and similar interactions via the N-terminus domain have been proposed for the chimera type galectins (Liu, 2000).

The galectins' ability to discriminate among carbohydrate structures is striking. Although galectins are β-galactoside-binding lectins, the relative binding affinity of either D-galactose or its α/β methyl derivative is almost 200 times less effective than that the β-galactose-containing disaccharide lactose (Lac) (Ahmed et al., 1990; 1996 a, b; 2004). For most galectins, N-acetyllactosamine (LacNAc) and thiodigalactoside (TDG) are 5-10 times more active than Lac. Close examination of carbohydrate-binding specificities of galectins, however, revealed diversity in their binding properties (Ahmed and Vasta, 1994). For example, the T-disaccharide is a good ligand for chimera galectins. The basis for the variable binding profiles of these galectins has been explained by their 3-D structures (Liao et al., 1994; Bianchet et al., 2000).

In the extracellular space, galectins bind to β-galactoside containing glycoproteins of ECM components and the cell surface adhesion molecules. These include laminin (Cooper et al., 1991; Zhou and Cummings, 1993), fibronectin (Ozeki et al., 1995), Thy-1 antigen (Symons et al., 2000), CD45 (Symons et al., 2000), $\alpha 7\beta 1$ integrin (Gu et al, 1994), $\alpha 3\beta 1$ integrin (Hadari et al., 2000), complement receptor CR3 (Avni et al., 1998), and Mac-2 binding protein (Rosenberg et al., 1991). However, the endogenous ligand of a particular galectin may vary from site to site (Leffler et al., 2004). In the intracellular space, galectins bind to their ligands, such as gemin 4 (Park et al., 2001), H-Ras (Paz et al., 2001), Bcl-2 (Yang et al., 1996), cytokeratin (Goletz et al., 1997), synexin (Yu et al., 2002) not only via protein-carbohydrate interactions, but also by protein-protein interactions. In the intracellular space, galectins are involved in mRNA splicing, cell cycle, cell proliferation, and apoptosis.

Galectins have been proposed to mediate diverse biological processes such as embryogenesis (Colnot et al., 1997; Ahmed et al., 2004), neuron projection (Puche et al., 1996), B cell development (Gauthier et al., 2002), inflammation (Liu, 2000, Rabinovich et al., 2002), apoptosis (Perillo et al., 1995, Hernandez and Baum, 2002), and tumor metastasis (Rubinstein et al., 2004; van den Brule et al., 2004; Liu and Rabinovich, 2005). The dynamic pattern of expression of gal1 and gal3 during mouse embryogenesis suggests that they have roles in notochord development, somitogenesis, development of central nervous system, and development of bone (Colnot et al., 1997, 2001; Gotz et al., 1997). The gal1 null mice are deficient in the development of a subset of olfactory neurons (Colnot et al., 1997).

Many epithelial tumors, such as colon, thyroid and breast carcinomas, express both gal1 and gal3. The increased expression of gal1 by tumor cells is positively correlated with a metastatic phenotype and a poorly differentiated morphology. Numerous reports indicate a direct correlation of gal3 expression with colon, head and neck, gastric, endometrial, thyroid and breast carcinomas, but some reports on colon and breast cancer present conflicting results (Nangia-Makker et al., 2002). gal2, 4, and 9 were confined to a significant fraction of colorectal tumor cell lines. gal1, 3 and 8 were involved in tumoral astrocyte invasion of the brain parenchyma (Camby et al., 2001). Ectopic expression of gal12 in cancer cells causes cell cycle arrest during G1 phase and cell growth suppression (Yang et al., 2001).

Although most galectins are ubiquitously expressed in various human tissues, in most cancers galectins were either upregulated or down-regulated relative to the normal parental tissue (van den Brule 2004). For example, gal1 is upregulated in thyroid cancer and uterine sarcoma (Xu 1995; Schwarz 1999), but its expression is decreased in head and neck cancer relative to the normal tissue (Choufani 1999). Similarly, expression of gal3 is found upregulated in gastric cancer (Lotan 1994), liver cancer (Hsu 1999), and thyroid cancer (Xu 1995), but its expression is down regulated in head and neck cancer (Choufani 1999) and uterine sarcoma (Schwarz 1999) compared to normal tissues. In prostate adenocarcinoma (PCa), the expression of gal3 is found decreased compared to normal prostate tissue (Ellerhorst 1999b; Pacis 2000). In contrast, the expression patterns of gal8 in prostate tumors are more complex (Su 1996; Danguy 2001). Expression of some proto type isoforms of gal8, such as gal8e and gal8g, is increased in the malignant prostate epithelial cells as compared to normal and benign cells (Ahmed 2007). However, some tandem-repeat isoforms of gal8, such as gal8a and gal8b, are equally expressed in normal, benign, and malignant prostate epithelial cells (Ahmed 2007).

Galectins are also involved in cellular functions like cell-cell aggregation, cell-matrix adhesion, and invasion processes that could be important during cancer progression and metastasis. Breast cancer cells expressing gal3 demonstrated adhesion to laminin and collagen IV, but not fibronectin (Warfield et al., 1997). In blood vessels, tumor cells form emboli (cell aggregates), which protects them in the hostile host environment. It was demonstrated that when induced by asialofetuin, cell surface gal3 mediates homotypic aggregation (tumor embolus) (Inohara and Raz, 1995). gal3 modulates integrin-ECM interactions. Integrins participate in intracellular signal transduction, which regulates cell proliferation, survival, differentiation, and motility (Mizejewski, 1999). gal3 is also present on the endothelial cell surface and contributes to metastasis (Glinsky et al., 2001). Metastasis of cancer requires extravasation of cells, which involves binding of cells to endothelium. It has been demonstrated that Thomsen-Friedenreich antigen (T antigen), which has β-galactose as the terminal residue, interacts with the endothelial gal3 (Glinsky et al., 2000). gal3 is involved in tumor related angiogenesis (Nangia Makker et al., 2000); it stimulates in vitro capillary tube formation by human umbilical endothelial cells (HUVEC) and in vivo neovascularization.

gal8 positively or negatively regulates cell adhesion, depending on the extracellular context (Levy et al., 2001). When immobilized onto ECM, gal8 promotes cell adhesion, spreading, and migration through selective interactions with α3β1 and α6β1 integrins. Cell adhesion to gal8 triggers integrin-mediated signaling cascades such as Tyr phosphorylation of focal adhesion kinase (FAK) and paxillin. In contrast, excess soluble gal8 interacts both with cell surface integrins and with other soluble ECM proteins and inhibits cell-matrix interactions (Zick et al., 2004).

Resistance to apoptosis enables tumor cells to avoid programmed cell death induced by detachment from the ECM, and to survive the host immune defenses during passage through the circulatory system. Several studies suggest an anti-apoptotic effect of gal3 in a variety of human tumor cells. Induction of gal3 expression in a human leukemia T cell line (Yang et al., 1996) and breast cancer cells (Akahani et al., 1997) was found to confer resistance to cell death. gal3 is the only member of the galectin family that contains the NWGR anti-death domain of the Bcl-2 family. Like Bcl-2, gal3 could be a mitochondria-associated apoptotic inhibitor (Matarrese et al., 2000), and a critical determinant for anchorage-independent and free radical-resistant cell survival during metastasis. Conversely, gal1 induces apoptosis of activated T cells and of both negatively selected and nonselected thymocytes (Perillo et al., 1998). Expression of gal1 protects tumor cells from immune surveillance by inducing the apoptosis of tumor infiltrating T cells (Rubinstein et al., 2004). Several human T cell leukemia lines are susceptible to gal1-induced apoptosis. Thus, although gal1 expression by carcinomas may favor tumor cell metastasis and a malignant phenotype, this protein may have therapeutic value for the treatment of hematopoietic malignancies because of its potential to induce apoptosis of leukemia cells (Perillo et al., 1998).

Initial screening of human primary prostate carcinoma revealed that gal1 was undetectable in normal, intraepithelial neoplasia or carcinoma cells, but present in the stroma, and associated fibroblasts (Van den Brule et al., 2001). Similarly, little or no expression of gal3 was observed in most prostate cancer cells. In those cases in which gal3 were detected, however, it was only in the cytoplasmic compartment (van den Brule et al., 2001). The role of gal3 in cancer progression was further examined by specifically expressing gal3 in either cytoplasm or nucleus of LNCaP, a gal3-negative human prostate cancer cell line (Califice et al., 2004). No changes in cell morphology, proliferation, attachment to laminin-1, or androgen dependency were observed. However, cytoplasmic gal3 significantly increased Matrigel invasion, anchorage-independent growth, in vivo tumor growth and angiogenesis, and decreased inducible apoptosis. Surprisingly, nuclear gal3 affected these parameters in an opposite fashion with an overall antitumoral activity (Califice et al., 2004). Several prostate cancer cell lines, including but not limited to PC-3, PC-3M, DU145, PrEC-1, and MCF10A express gal3, whereas LNCaP and TSU-pr1 do not.

Figure 3:
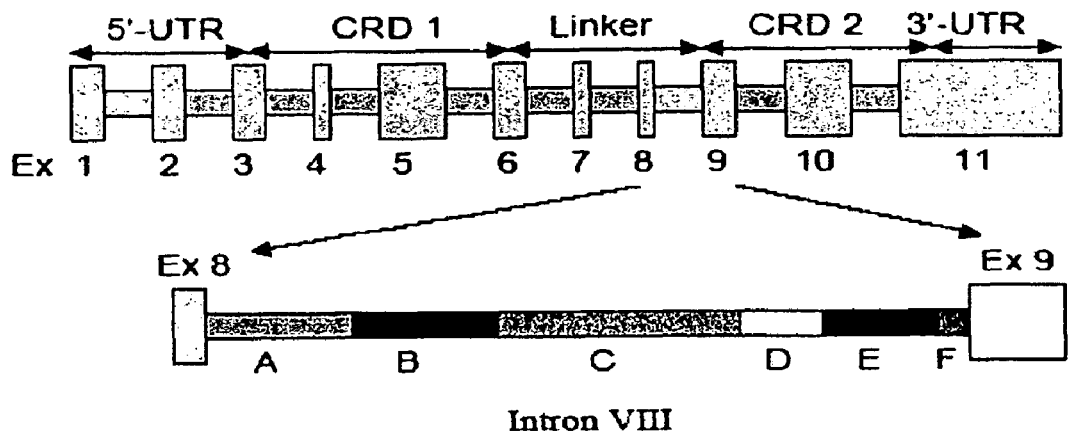
FIG. 3 shows gene organization of human gal8. Schematic representation of gal8 gene and cDNAs for several isoforms of gal8. Isoforms (three tandem-repeat type gal8a to gal8c and four proto type gal8d to gal8g) are produced by alternate splicing of intron VIII. The arrow in gal8d to gal8g indicates the stop codon. Alternative names for gal8 isoforms are based on Su et al. (1996) and Bidon et al. (2001).
Figure 3:
Figure 3:
Figure 3:
Figure 3:
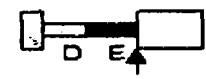
Figure 3:
Figure 3:

Results relating to the assessment of gal8 expression in cancer cells are conflicting, but may be based on transcript heterogeneity. One study indicates that gal8, also known as prostate carcinoma tumor antigen-1 (PCTA-1; identified by surface-epitope masking and expression cloning) is selectively expressed in prostate cancer cells, but not in normal prostate or benign hyperplasia (Su et al., 1996). In contrast, gal8 has been reported as expressed at low levels in normal tissues as well as benign hyperplasia or adenocarcinoma by histochemistry (Danguy et al., 2001). This notion is supported by the results from Cancer Genome Anatomy Project (CGAP) library analysis (hyper text transfer protocol address cgap.nci.nih.gov/). The conflicting data on gal8 expression are most likely due to the complexity of gal8 structures, the diversity of isoforms as shown in FIG. 3, and the type of probes used in those studies. The gal8 gene encodes numerous mRNAs by alternate splicing mostly on intron VIII (Bidon et al., 2001). These mRNAs encode six different isoforms of gal8; three belong to the tandem-repeat type (containing two CRDs) and three to the proto type group (one CRD).

Figure 4:
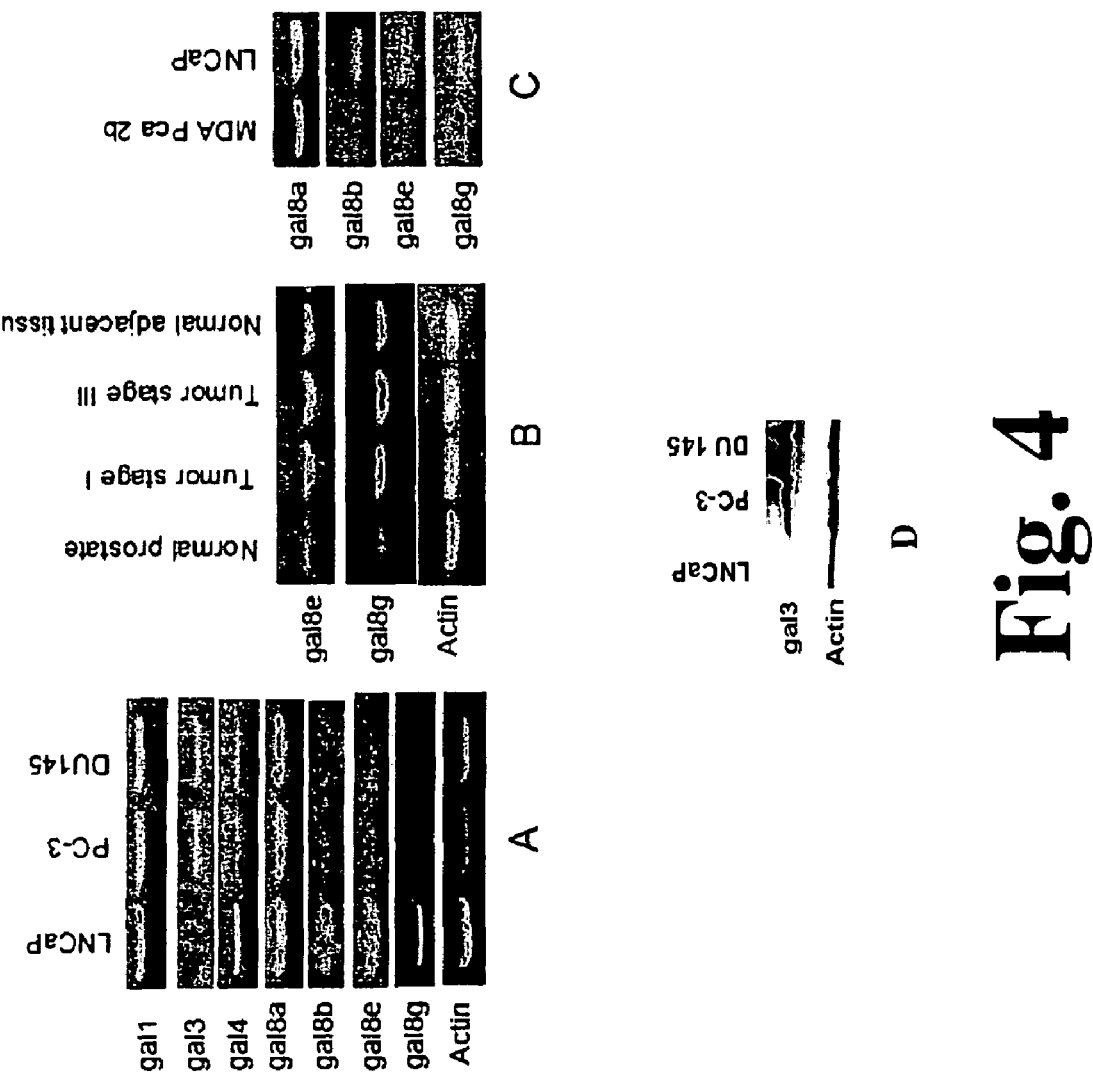
FIG. 4 shows results of RT-PCR analysis and Western Blot. Galectin expression in LNCaP, PC-3 and DU145 cell lines (A), prostate tissues (B), MDA PCa 2b cell line (C) and Western Blot (D) of gal3 expression in LNCaP, PC-3 and DU145 cell lines.

A novel gal8 mRNA transcript has been discovered by the present inventors and discussed herein, which results in a distinct proto type isoform (gal8g) as shown in FIG. 3. Analysis of this transcript reveals a stop codon at the beginning of the spliced intron VIII, yielding a proto type isoform of gal8 (gal8g), which is different from all previously known proto gal8 isoforms (Bidon et al., 2001; Bidon-Wagner and Le Pennec J P, 2004). To confirm the authenticity of the gal8g, gene specific primers were designed from its non-overlapping sequence (beginning of the intron VIII, see FIG. 3) and a gene specific product was amplified from LNCaP cell and prostate tissues (see later). It was found that these high levels of expression of gal8g in the androgen dependent (AD) cell line LNCaP, but little or no expression in the androgen independent (AI) cell lines PC-3 and DU145, as shown in FIG. 4A.

DNA methylation is an enzyme-mediated chemical modification that adds methyl ($CH_3$) groups at selected sites of DNA. In mammals, DNA methylation is the only known natural modification of DNA and affects the cytosine (C) when it is followed by a guanosine (G). Thus, in mammals, DNA methylation occurs at CpG sites. In human, 70-80% of all CpG sites are methylated (world wide web address mdanderson.org). Epigenetic alterations including hypermethylation of gene promoters are proved to be early events in neoplastic progression (Hanahan and Weinberg, 2000; Warnecke and Bestor, 2000). Promoter hypermethylation of tumor suppressor genes is known to contribute to the silencing of their expression during the neoplastic process (Jones and Baylin, 2002) and thus, these methylated genes can serve as biomarkers for the detection of cancer (Fackler et al., 2004). However, methylation of these genes correlates positively with tumor grade and stage (i.e. low methylation in early stages and high methylation in late stages (Jeronimo et al., 2004))

and thus an assay based on the measurement of methylation of these genes are not suitable for the detection of early stages of prostate cancer.

Abnormal gal1 expression has been found during cell dedifferentiation, and in neoplastic cells. A small genomic region of approximately 100 base pairs surrounding the transcriptional start site (−50/+50) accounts for most transcriptional activity of gal1 (Salvatore et al., 1998). Using the bisulfite genomic sequencing technique (bisulfite converts unmethylated C to U), it was found that the mechanism that mainly controls the cell-specific expression and the reactivation of gal1 gene is the transition from a fully methylated to a fully unmethylated state of 11 CpG sites near the transcription start site (Benvenuto et al., 1996). Also, in normal mouse and rat tissues the rate of DNA methylation of the small CpG island surrounding the start correlates with transcription activity (Salvatore et al., 1998). Recently, Kondoh et al. (2003) demonstrated that the activation of gal1 gene in human hepatocellular carcinoma involves methylation-sensitive complex formations at the transcriptional upstream and downstream elements. The gal3 start site lies in the middle of a large CpG island and thus DNA methylation could be one of the mechanisms governing gal3 gene expression (Chiariotti et al., 1999). The expression of gal3 gene was found silenced by methylation of its promoter in murine melanoma cells (Costa et al., 2003). However, similar gene silencing mechanisms for gal8 by promoter methylation was heretofore unknown.

To determine levels of expression in different cells and tissues, expression of gal1, 3, 4, and 8 was characterized in PC cells and prostate tissues (normal and tumor) by RT-PCR. gal1 was expressed in all PC cells tested as shown in FIG. 4A. gal3 was highly expressed in the AI cell lines PC-3 and DU145, but weakly expressed in the AD cell line LNCaP. Expression of gal4 in LNCaP was intense, but weak in both PC-3 and DU145. Expression of gal8 isoforms is intriguing: the newly discovered proto isoform gal8g is highly expressed in LNCaP, but not expressed in either PC-3 or DU145. Similar results were obtained with gal8b (also known as Po66-CBP-IS1) and gal8e (also known as Po66-CBP-IS1-IS2). However, gal8a (also known as PCTA-1 and Po66-CBP) is equally expressed in all three cell lines. The other gal8 isoforms (gal8c, gal8d, and gal8f) were not detected in the RT-PCR studies.

Normal and tumor prostate tissues (RNAs obtained from Ambion, Austin, Tex.) were analyzed by RT-PCR for galectin expression and the results shown in FIG. 4B. The expression of either gal8e or gal8g in stage III tumor (T3N0M0, grading and tumor staging according to the AJCC classification) was higher than that in stage I (TiN0M0), although expression in both tumor cell types was still higher than that in normal prostate or normal adjacent tissue.

It is noteworthy that another AD PC cell line, MDA PCa 2b, which originates in a bone metastasis, shows expression of gal8a similar to LNCaP; but unlike LNCaP, it shows little or no expression of gal8b, gal8e, and gal8g as shown in FIG. 4C. These results indicate that expression of galectins in PC cells does not correlate with their AD properties, but rather relate to their aggressiveness (non-metastatic versus metastatic).

Figure 5:
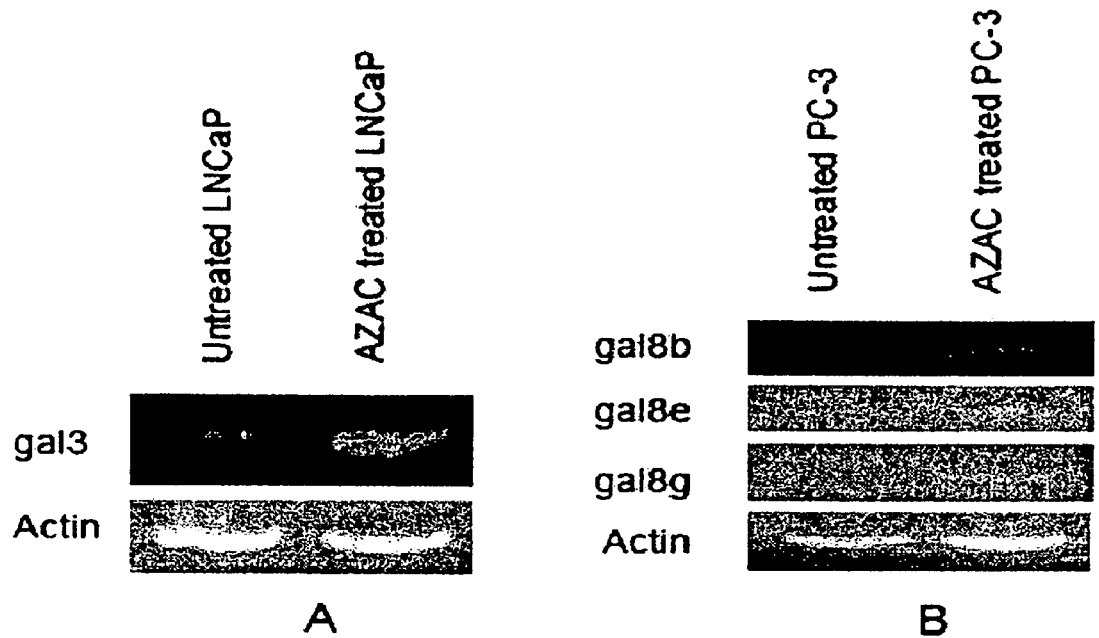
FIG. 5 shows expression of gal3 in azacytidine-treated LNCaP (A) and gal8 isoforms in azacytidine-treated PC-3 cells (B).

As shown in FIGS. 4A and D, the gal3 gene is highly expressed in PC-3 and DU-145, but silent in LNCaP. In contrast, most gal8 isoforms except gal8a are silent in PC-3 and DU145. The present inventors determined that DNA methylation of galectin genes is responsible for galectin gene silencing. Since azacytidine blocks cytidine methyl transferase activity, treatment of cells with azacytidine should reactivate the genes. Treatment of LNCaP and PC-3 cells was accomplished by adding 10 uM 5-aza-2'-deoxycytidine daily for five days to the culture medium. RT-PCR was then performed on RNA extracted from the treated PC cells. Azacytidine-treated LNCaP showed expression of gal3 as shown in FIG. 5A. Similarly, AZAC-treated PC-3 showed expression of gal8b, gal8e, gal8g by RT-PCR as shown in FIG. 5B. These results indicate that gal3 and gal8 promoters may be methylated in LNCaP and PC-3 cells, respectively.

Figure 6:
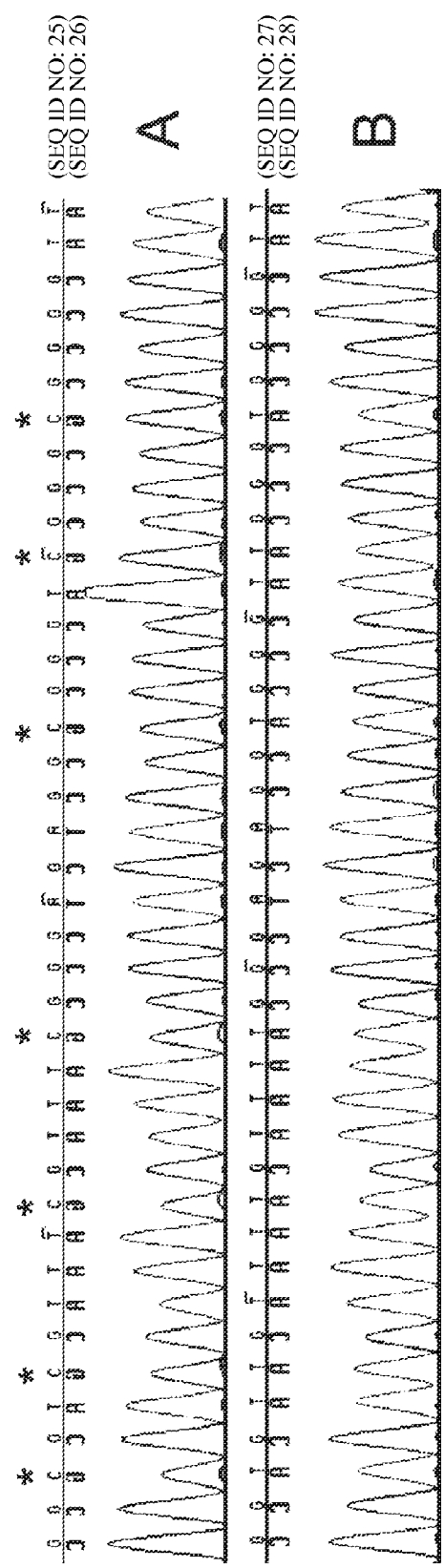
FIG. 6 shows sequencing chromatogram of bisulfite treated DNA. A. Partial chromatogram showing cytosine methylation (indicated by asterisks) of the gal3 promoter in LNCaP. The sequence shows two CpG islands (−73 to −34 nt) (Kadrofske et al., 1998). B. The gal3 promoter sequence is either from PC-3 or DU 145 or human placenta. Note that all nucleotides (in B) corresponding to the methylated C (in A) have changed to T, which represents U in the promoter.
Figure 7:
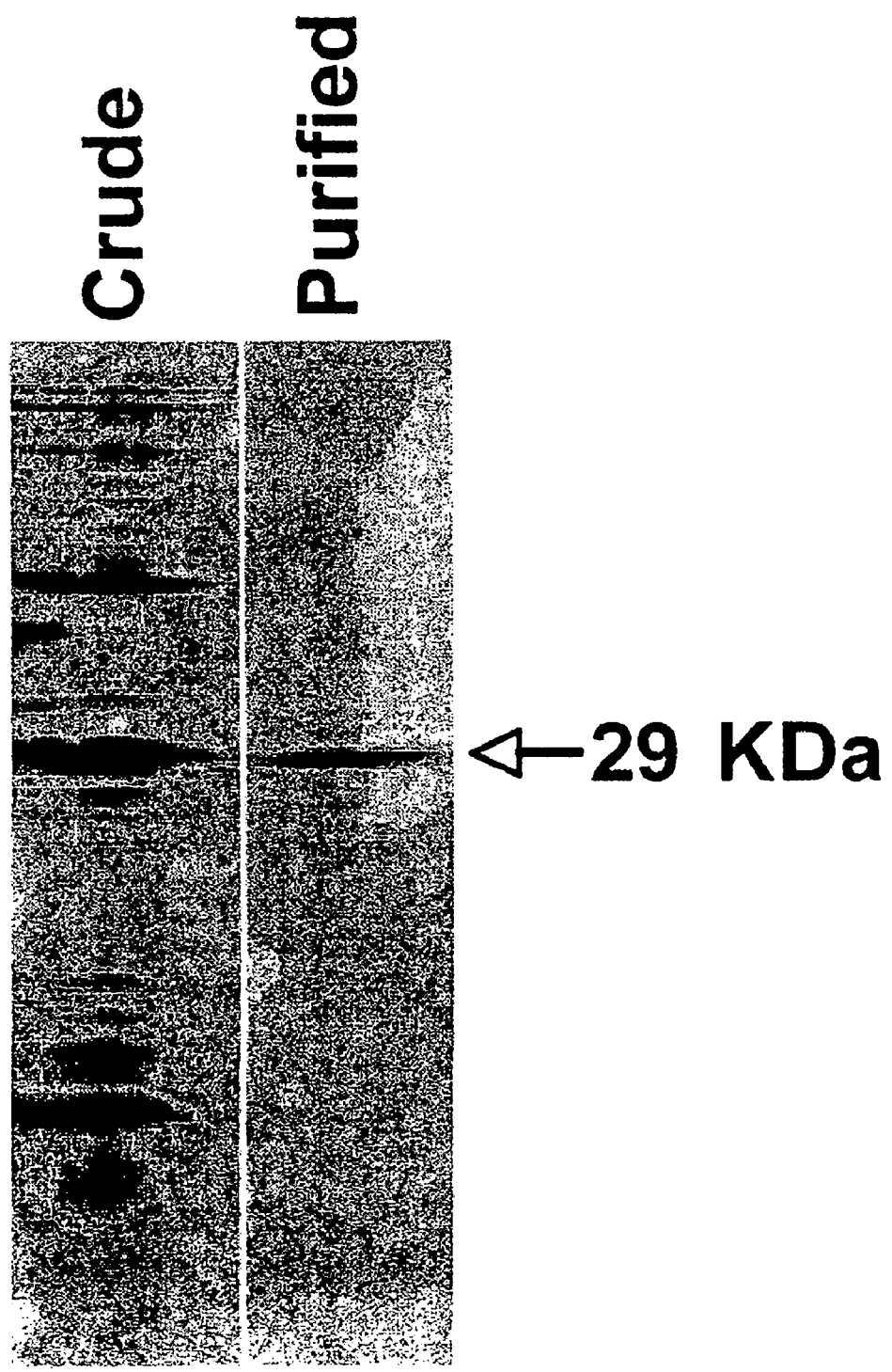
FIG. 7 shows a blot of purification of human recombinant gal3.15% SDS-PAGE of the lactosyl-Sepharose purified gal3.
Figure 8:
FIG. 8 is a blot showing the specificity of anti-gal3 antibodies. Crude cell extract (MC3T3E1) was tested with the anti-galectin-3 antibodies on western blot.
Figure 12:
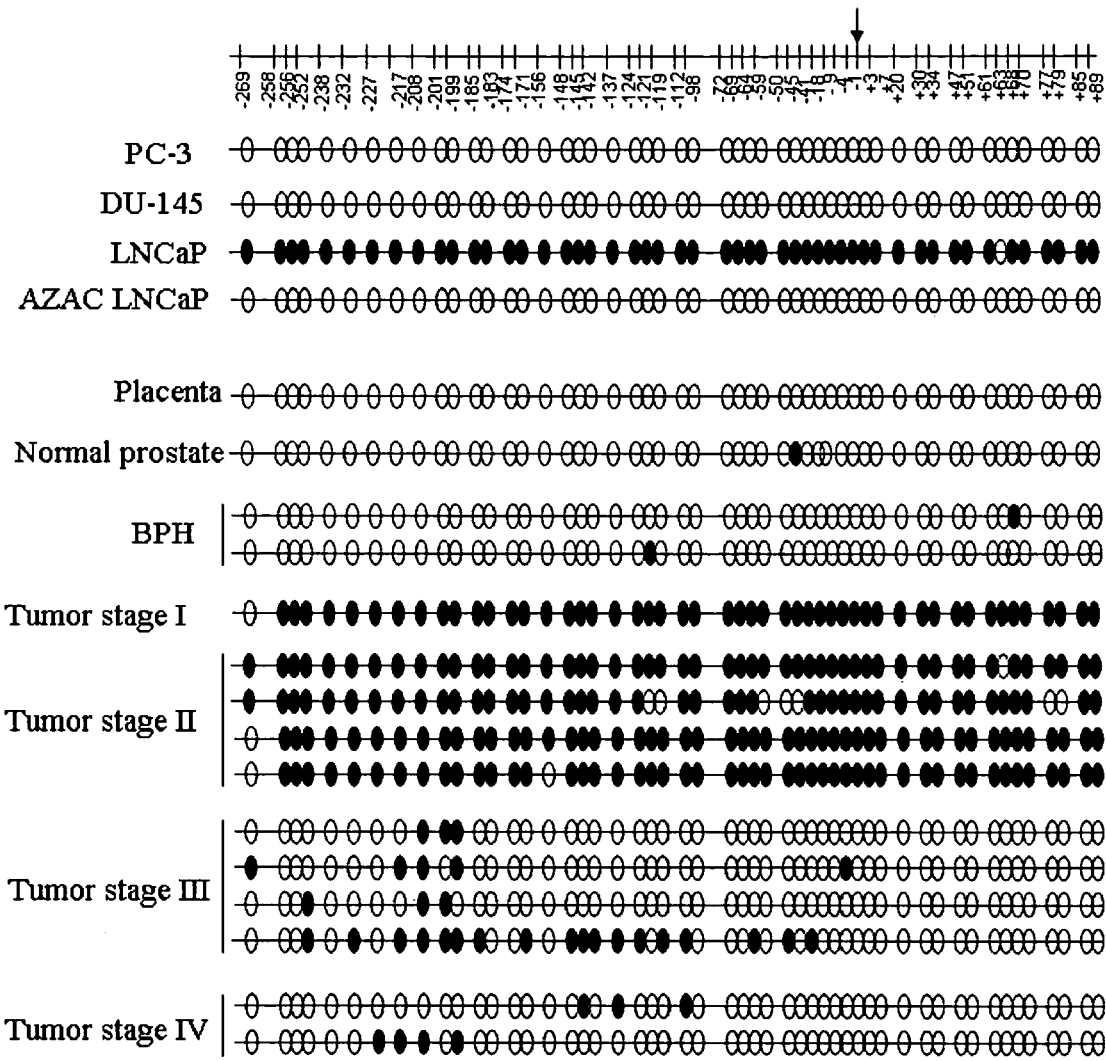
FIG. 12 illustrates the methylation profile of the gal3 promoter from DNA samples obtained from LNCaP, PC-3, DU145 and Azac-treated DU145 cell lines, as well as placenta, normal prostate, BPH, Stage I tumor, Stage II tumor, Stage III tumor and Stage IV tumor cells.

Bisulfite genomic sequencing allows precise analysis of methylation in a certain region by converting all non-methylated cytosines (C) into uracil (U) by bisulfite treatment, while methylated cytosines remain unchanged. DNA was obtained from LNCaP, PC-3, DU145 and Azac-treated DU145 cell lines, as well as placenta, normal prostate, BPH, Stage I tumor, Stage II tumor, Stage III tumor and Stage IV tumor cells. 500 ng of DNA from the cell lines or tissues was treated with sodium bisulfite by EZ Gold Methylation kit (Zymo Research, Orange, Calif.) and subsequently amplified by PCR (CD-PCR; Frommer et al., 1992) with primer pairs located outside the CpG sites, using the Multiplex PCR kit (Qiagen Inc., Valencia, Calif.). The primers for gal3, after taking into account the bisulfite conversion reaction were: (a) forward primer (HuG3BPF3), 5'-GGAGAGGGTGGGG-GAT-AG-3' (SEQ ID NO: 9) derived from the wild-type sequence 5'-GGAGAGGGCGGGGGACAG-3' (SEQ ID NO: 10) (ranging from −277 to −260 nt of the promoter sequence, 20); and (b) reverse primer (HuG3BPR3), 5'-ACACCCTCTCCCCTACCC-3' (SEQ ID NO: 11) derived from the wild-type sequence 5'-GCGCCCTCTCCCTGCCC-3' (SEQ ID NO: 12) (ranging from +90 to +107 nt of the promoter sequence). The PCR product was cloned into a pGEM-T vector (Promega) and sequenced. All cytosines of CpG sites (about 50) in the gal3 promoter from LNCaP DNA were methylated in the 384 bp PCR product (FIG. 6 and FIG. 12), but no gal3 promoter methylation was observed in azacytidine-treated LNCaP. Similarly, no methylation of the gal3 promoter from either PC-3 or DU 145 DNA was observed. In FIG. 12, each row represents a single cloned allele of gal3, and each oval represents a single CpG site (open oval, non methylated; closed oval, methylated). The numbering in the schematic diagram at the top represents the position relative to the published transcription site (+1, indicated by the arrow). For each sample, at least 20 clones were sequenced. Two representative sequences for each of BPH and tumor stage IV, and four representative sequences for each of stage II and III were shown Human gal3 recombinant protein was expressed in E. coli from a construct placed into the pET vector (Novagen, Madison, Wis.). The recombinant galectin was purified on a lactosyl-Sepharose column as shown in FIG. 7. gal8a and gal8g were also cloned into pET vector for recombinant expression of the tandem-repeat and proto type proteins, respectively. The purified recombinant gal3 and gal8a are used to raise antibodies and used as antigens in immunoassays. Specifically, the purified recombinant gal3 was used to raise antibodies in rabbits (Duncroft, Lovettsville, Md.). The antiserum titer was determined by ELISA as previously described (Ahmed et al., 2004), and its specificity assessed by western blot of MC3T3E1 (mouse calvaria-derived osteoblasts) cell extract as shown in FIG. 8. This antibody can be used for immunostaining of gal3 in normal and tumor tissues as well as in immunoassay and western blot to identify gal3 in sera from healthy individuals and prostate cancer patients. In order to generate specific antibodies against gal8g, a non-overlapping peptide not encoded by any other known gal8 variant (beginning of spliced intron VIII, see FIG. 3) is used to immunize rabbits.

PCR products specific for gal3 and gal8g (non-overlapping oligonucleotides not encoded by any other known gal8 variant, at the beginning of spliced intron VIII, see FIG. 3) were cloned into a pGEM-T vector (Promega, Madison, Wis.) and linearized by restriction digest with either SacII or SpeI. Antisense and sense RNA probes were synthesized by incorporating digoxigenin-UTP (Roche, Indianapolis, Ind.) using T7 and SP6 RNA polymerase (Promega) as previously described (Ahmed et al., 2004).

The rigorous characterization of the galectin expression in various stages of prostate cancer tissues, normal prostate tissues, and BPH tissues is critical for development of biological markers for diagnosis and prognosis of prostate cancer, thus expression of gal3 and gal8 is investigated in normal and tumor prostate tissues by RT-PCR, Northern analysis, western blot, and quantitative real time PCR. Biopsy samples from various stages of tumors (RNAs are commercially available from Ambion, Austin, Tex.) are examined for galectin expression by RT-PCR and quantitative real time PCR. Normal and tumor prostate tissues and BPH tissues (using slides that are commercially available from TeleChem International, Inc., Sunnyvale, Calif.) are examined for in situ hybridization and immunostaining. It is known that galectins are secreted to serum (Iurisci et al., 2000) and these galectins in sera from healthy human and prostate cancer patients is examined by westernblot and immunoassays. For immunostaining, antibodies are raised against selected galectins, preferably gal3 and gal8g. Recombinant galectins will be expressed into E. coli. In order to generate gal8g specific antibodies, non-overlapping peptides are used.

Galectins are differentially expressed in various stages of prostate cancer (Pacis, et al., 2000; see also Examples, below). From the examples below, it is seen that expression of gal3 is dramatically decreased in stage I and II prostate cancer, relative to the normal and BPH prostate tissue. Its expression returns in stage III and IV prostate cancer, but levels remain low as compared to the normal tissue. The examples demonstrate that in stage I and II prostate cancer the gal3 promoter is heavily methylated (see Examples, below). The gal3 promoter in stages III and IV of prostate cancer was found to be only lightly methylated, and virtually no methylation could be detected in normal and BPH tissues (see Examples, below).

The heavy methylation of the gal3 promoter in the early stages of prostate cancer is in contrast to other genes, which are not methylated in the early stages. Thus gal3 is found to be a marker for early diagnosis of prostate cancer.

Figure 10:
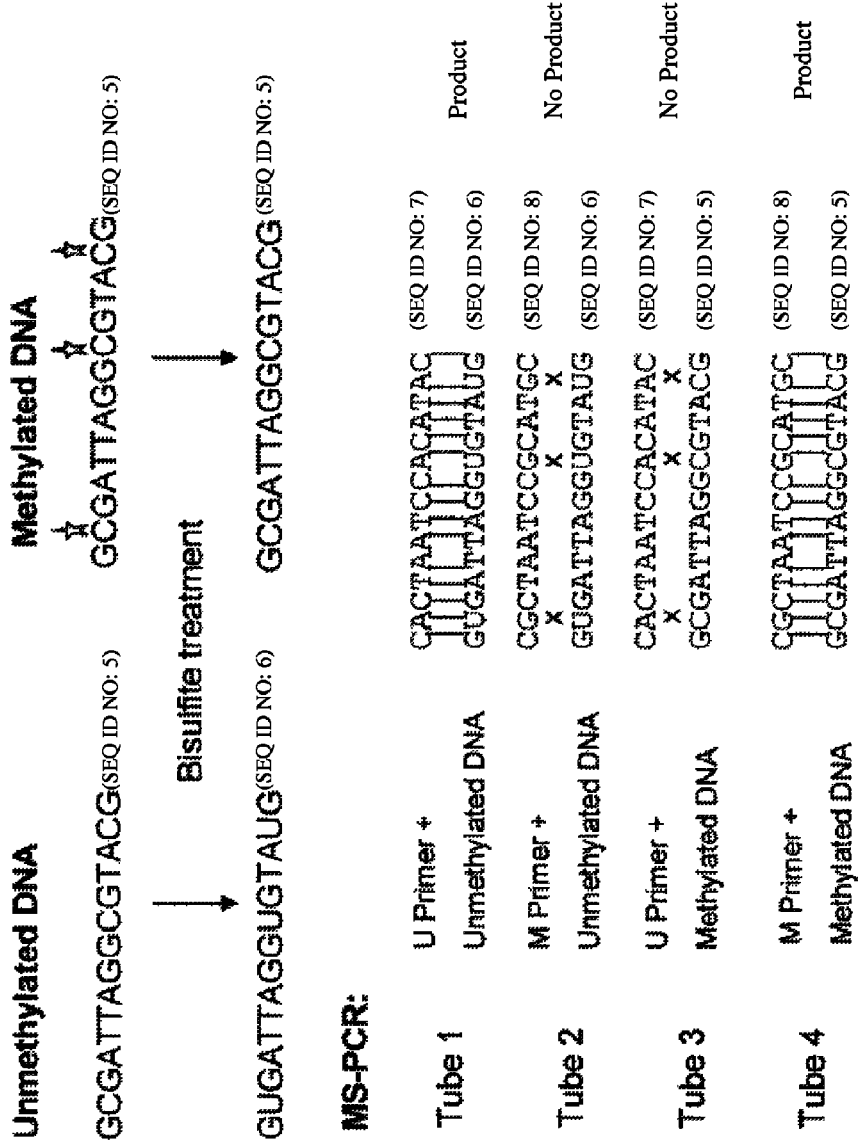
FIG. 10 is a schematic representation of MS-PCR.
Figure 11:
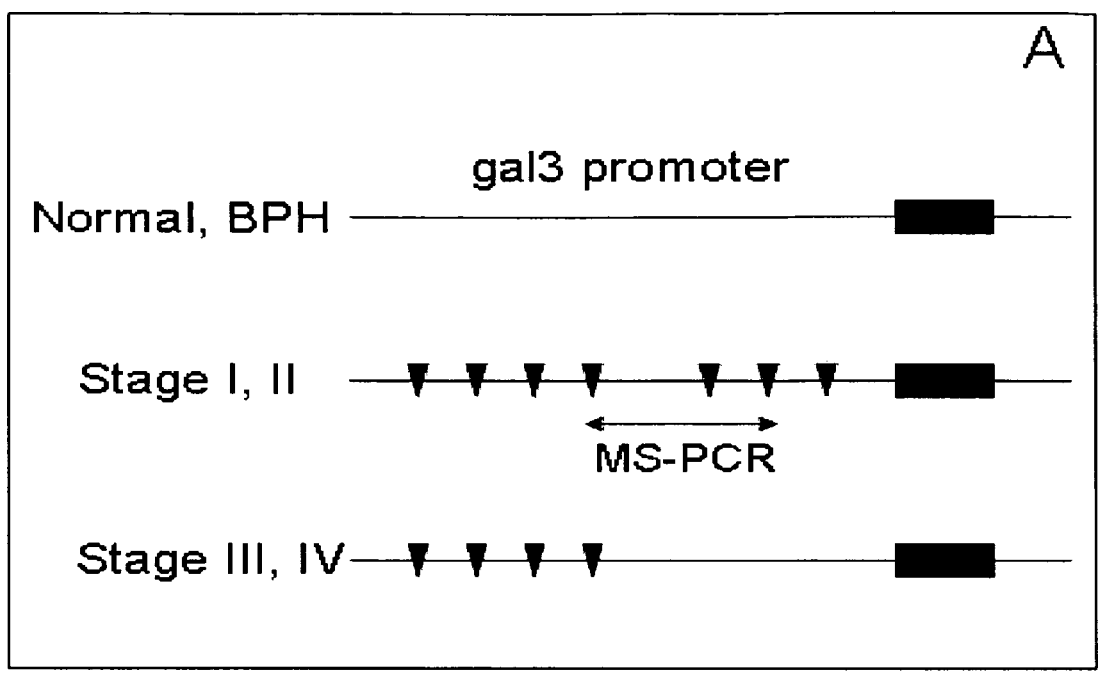
FIG. 11 is a schematic representation of the methylation of the gal3 promoter in Normal, BPH, Stage I, II, III and IV cancer prostate tissues.

The present discovery of differential cytosine methylation in the gal3 promoter in stages I-IV of prostate cancer enabled development of a methylation specific PCR-based sensitive assay (MS-PCR) specific for stage I and II (FIG. 10). In the examples below, using normal, BPH, and prostate cancer tissues as well as serum and urine samples of various prostate cancer stages, the MS-PCR assay is shown to reliably detect early stages of prostate cancer with 100% sensitivity.

In particular, Examples 3 and 4 demonstrate that MS-PCR with the gal3 methylated primers identified all stage I and II samples from PC patients. PCR with the unmethylated primers were positive in all samples indicating the presence of unmethylated gal3 DNA. The presence of unmethylated DNA allele in the prostate cancer specimens may be due to the fact that the tissue sample is heterogeneous in tumor content.

In contrast to genes previously employed as prostate cancer markers, the gal3 promoter is fully methylated in stage I and II prostate cancer, thereby providing the basis of the presently described non-invasive assay for the detection of early stages of prostate cancer. In one embodiment the invention provides that gal3 MS-PCR can reliably detect all stage I and II samples from PC patients.

Figure 16:
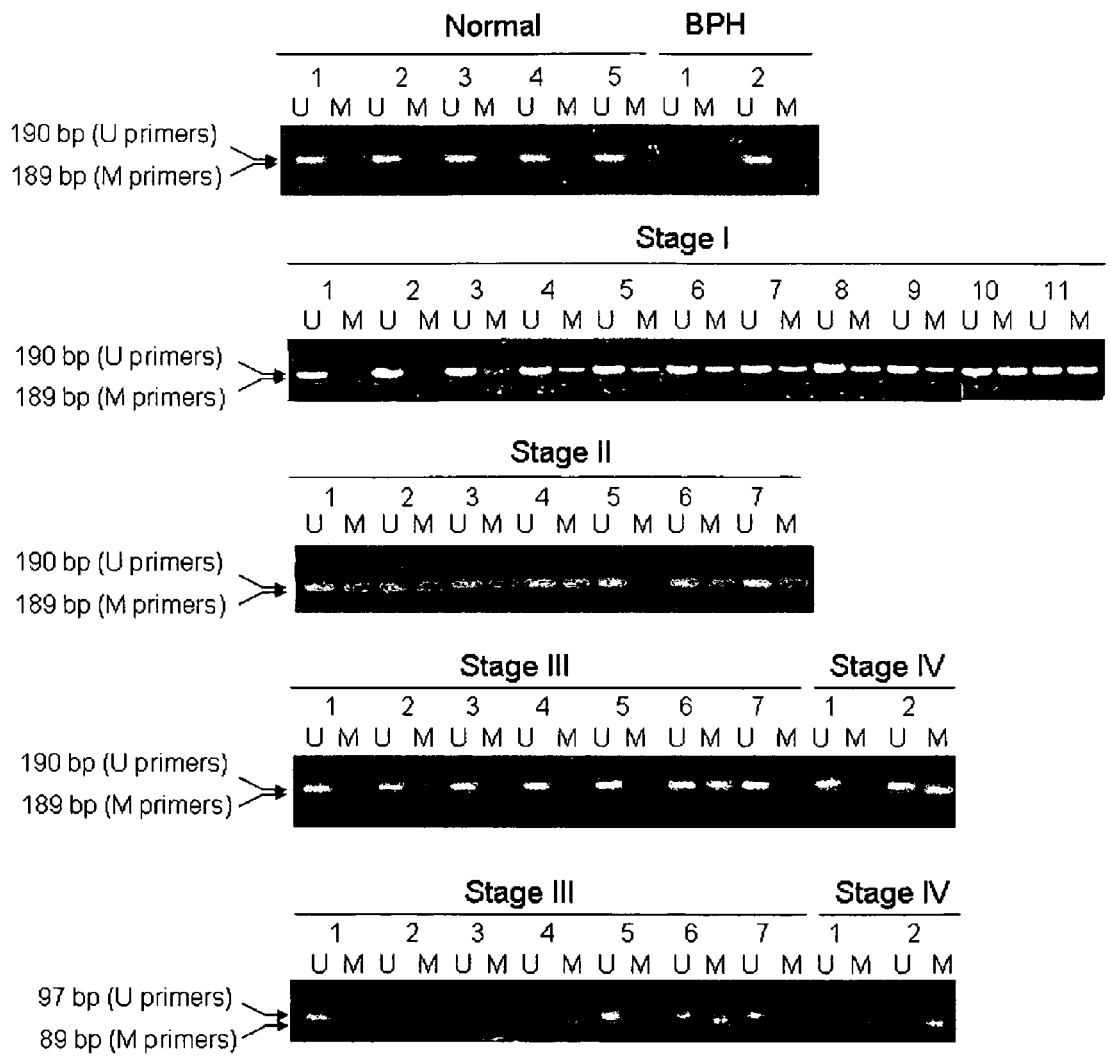
FIG. 16 shows PCR of bisulfite-treated DNA isolated from normal, BPH, and tumor prostate tissues with GSTP1 unmethylated (U) and methylated (M) primer pairs. The products 190 bp and 189 bp obtained from unmethylated and methylated primer pairs, respectively, are shown by arrows. The bottom panel shows bisulfite-treated DNA from stage III and IV tumors subjected to PCR with a second pair of unmethylated (expected product size 97 bp) and methylated (expected product size 89 bp) primers from GSTP1 promoter.

Examples 5 and 6 illustrate us of glutathione S-transferase P1 (GSTP1) as an additional marker in the identification of prostate cancer. An additional MS-PCR assay was developed, based on the methylation pattern of the glutathione S-transferase P1 (GSTP1) gene to identify prostate cancer (stages III and above) (see Example 5; FIG. 16). Methylation of GSTP1 correlates positively with tumor grade and stage (i.e. low methylation in early stages and high methylation in late stages, 18). However, a method based solely on GSTP1 promoter methylation is not suitable to identify prostate cancer at early stages, such as stage I and II (sensitivity 50%, specificity almost 100%) (Hoque et al., 2005).

Accordingly in another embodiment the invention provides an assay detecting both gal3 and GSTP1, with sensitivity to all of Stages I-IV prostate cancer. Such detection is set forth below in Example 6, where detection of methylated gal3 and GSTP1 DNA from early stages of prostate cancer was performed in biological fluids such as serum and urine.

Results of the methods of Example 6 indicate that the gal3 and GSTP1 MS-PCR assays together reliably identified both early and advanced stage prostate cancer, including 100% sensitivity for stage II.

Example 7 provides an additional assay based on the methylation pattern of the GSTP1 gene to identify prostate cancer of stages III and above and the methylation pattern of the gal3 gene to identify stages I and II. The assay of Example 7 provides a quantitative assay platform that combines MS-PCR assays for gal3 and GSTP1 methylation which will serve as a powerful diagnostic tool to reliably identify prostate cancer.

As shown in detail herein, prostate tissue samples are positive for gal3 and/or GSTP1 methylation in samples from PC-containing patients. Serum and urine are known to have significant amounts of circulating small DNA (Botezatu et al., 2000; Anker et al., 2001). Additionally, serum and urine samples are shown be to positive for gal3 and/or GSTP1 methylation in samples from PC-containing patients and are therefore effective for use in detection of prostate cancer. Similarly it is an embodiment of the invention that the non-invasive diagnostic method of detection of early stages of prostate cancer can be performed on other bodily fluids, including, but not limited to saliva.

The following examples are intended to illustrate, but not limit the invention.

Example 1

Detection of Galectin Methylation

RT-PCR is performed on tissue RNAs (available from Ambion) using the Reverse Transcription System (Promega, Madison, Wis.) following the manufacturer's instructions. For expression of gal3 and gal8g genes, custom primers specific to each galectin are made by Invitrogen (Carlsbad, Calif.). For RNA integrity and loading control, β-actin is used and amplified. PCR is performed in a PTC-200 thermal cycler from MJ research (Waltham, Mass.) using the protocols previously described (Ahmed et al., 2004).

As discussed above, results show a distinct expression pattern of galectins in PC cells. Most notably, gal3 is highly expressed in AI cell lines PC-3 and DU145, but show little or no expression in AD cell line LNCaP as shown in FIG. 4A. In contrast, most isoforms of gal8 are expressed in LNCaP, but exhibit little or no expression in PC-3 and DU145.

Total RNA (20 ug) is resolved in a 1% agarose/6% formaldehyde gel, transferred to nylon membranes and probed for various galectins. The gene specific DNA probes are prepared by random-primed reactions using partial or complete coding sequence of galectin cDNA.

In situ hybridization and immunostaining is carried out following the protocols previously described (Ahmed et al., 2004). Antisense and sense probes have been developed for gal3 and gal8g for in situ hybridization. Specific anti-gal3 antibodies have been developed to be used for immunostaining. Biopsy slides, each containing about 84 spots of various stages of prostate cancer, BPH, PIN, and normal prostate, are purchased from TeleChem International, Inc. (Sunnyvale, Calif.). Moreover, tissues of various stages of prostate tumor are obtained from the Cooperative Human Tissue Network (National Cancer Institute) and the National Disease Research Interchange (Philadelphia, Pa.).

In the present invention, gal3 was highly expressed in PC-3 and DU145, but showed little or no expression in LNCaP. In contrast, several galectin-8 isoforms were found in LNCaP, but with little or no expression in PC-3 and DU145 (see FIG. 4). However, azacytidine-treated LNCaP and PC-3 cells showed expression of gal3 and gal8 isoforms, respectively (see FIG. 5). Azacytidine blocks cytidine methyltransferase activity.

To determine the level of methylation, cytosine deamination of single-stranded DNA by bisulfite treatment is performed. Genomic DNA from normal, BPH, and tumor tissues are prepared using the NucleoSpin Genomic DNA extraction kit (Macherey-Nagel Inc., Bethlehem, Pa.) following the manufacturer's instructions. Genomic DNA from normal prostate and tumor prostate tissues has also been purchased from Ambion (Austin, Tex.). Genomic DNA from human placenta (Sigma) is used as a control. Genomic DNA (8 ug) is digested with XbaI and then denatured in 0.3 M NaOH for 15 min at 37° C. in a volume of 100 ul, and then 60 ul of 10 mM hydroquinone and 1.04 ml of 3.6 M sodium bisulfite (pH 5) is added. The reaction mixture is incubated at 50° C. for 16 h in the dark. The DNA is purified with a desalting column (Magic DNA Clean-Up System; Promega), denatured with 0.3 M NaOH for 15 min at 37° C., neutralized with 3 M ammonium acetate (pH 7), and ethanol precipitated. An aliquot of DNA is amplified by using modified primers (see below). All PCRs is carried out in 50-ul volumes containing 10 mM Tris, 50 mM KCl, 3 mM $MgCl_2$, 5% dimethyl sulfoxide, 0.2 mM deoxynucleoside triphosphates, 5 pmol of each primer, and 1 U of Taq polymerase (Stratagene) as previously described (Ahmed et al., 2004). The amplified fragments are cloned into the pCRII vector of the TA cloning system (Invitrogen), and at least 20 independent clones for each fragment are sequenced by using T7 primer (Novagen) to determine the methylation pattern. The primers for gal3 after taking into account the bisulfite conversion reaction are: (a) forward primer (HuG3BPF1), 5'-TAAGGTGGAAGTGGTAAGGGG-3' (SEQ ID NO: 1) derived from the wild-type sequence 5-CAAGGTGGAAGTGGCAAGGGG-3' (SEQ ID NO: 2); and (b) reverse primer (HuG3BPR1), 5'-CCCCACACAACT-CACCACTC-3' (SEQ ID NO: 3) derived from the wild-type sequence 5'-CCCCGCGCAGCTCACCGCTC-3' (SEQ ID NO: 4). The primers are chosen from the area outside the CpG islands. Similarly, primers for methylated and unmethylated gal8 promoter are made and PCR amplification is performed. Cytosine methylation is shown in gal3 promoter in LNCaP. Various degrees of methylation of gal3 are shown in various stages of prostate cancer.

It was found that gal3 and gal8g are differentially expressed in various stages of prostate cancer as shown in Table 1. Expression of gal3 is dramatically decreased in stages I and II PC relative to the normal tissue, and although its expression is slightly increased in stage III PC, it is still lower than normal (Pacis et al., 2000). In contrast, gal8 is highly expressed in PC, but not in normal prostate or BPH (Su et al., 1996). Results of differential expression of galectins and cytosine methylation of their promoters in various stages of PC are the basis of this described differential assay.

Table 1 also demonstrates the methylation of gal3 and gal8 in various stages of prostate cancer, where methylation of the gal3 promoter is indicated as heavily methylated in stages I and II PC relative to the normal tissue, and although it is lightly methylated in stages III and IV PC, it is still higher than normal. Specifically, with regard to the results reported in Table 1 for gal3, 51 CpG sites were examined for methylation. In the Stage I sample, 50 of 51 sites were found to be methylated, demonstrating 98% methylation. In the Stage II sample, 50 of 51 sites were found to be methylated, demonstrating 98% methylation. In the Stage III sample, 3-21 of 51 sites were found to be methylated, demonstrating 6-41% methylation. In the Stage IV sample, 3-4 of 51 sites were found to be methylated, demonstrating 6-8% methylation. The methylation results are illustrated comparatively in Table I, showing methylation in BPH and PIN samples as equal to (=) the methylation of normal samples, methylation in Stages I and II samples to be heavy (>>) as compared to normal tissue and methylation in Stages III and IV samples to be increased (>) as compared to normal tissue, but not as heavy as Stages I and II.

Further, because galectins are secretory and are found in serum and body fluids (Su et al., 1996; Iurisci et al., 2000), these body fluids constitute an ideal target for the development of diagnostic assays for PC. Furthermore, reliable semi- or quantitative methods for assessing levels of these markers in urine constitutes the ideal non-invasive methods for PC diagnosis to be applied at the doctor's office.

Figure 9:
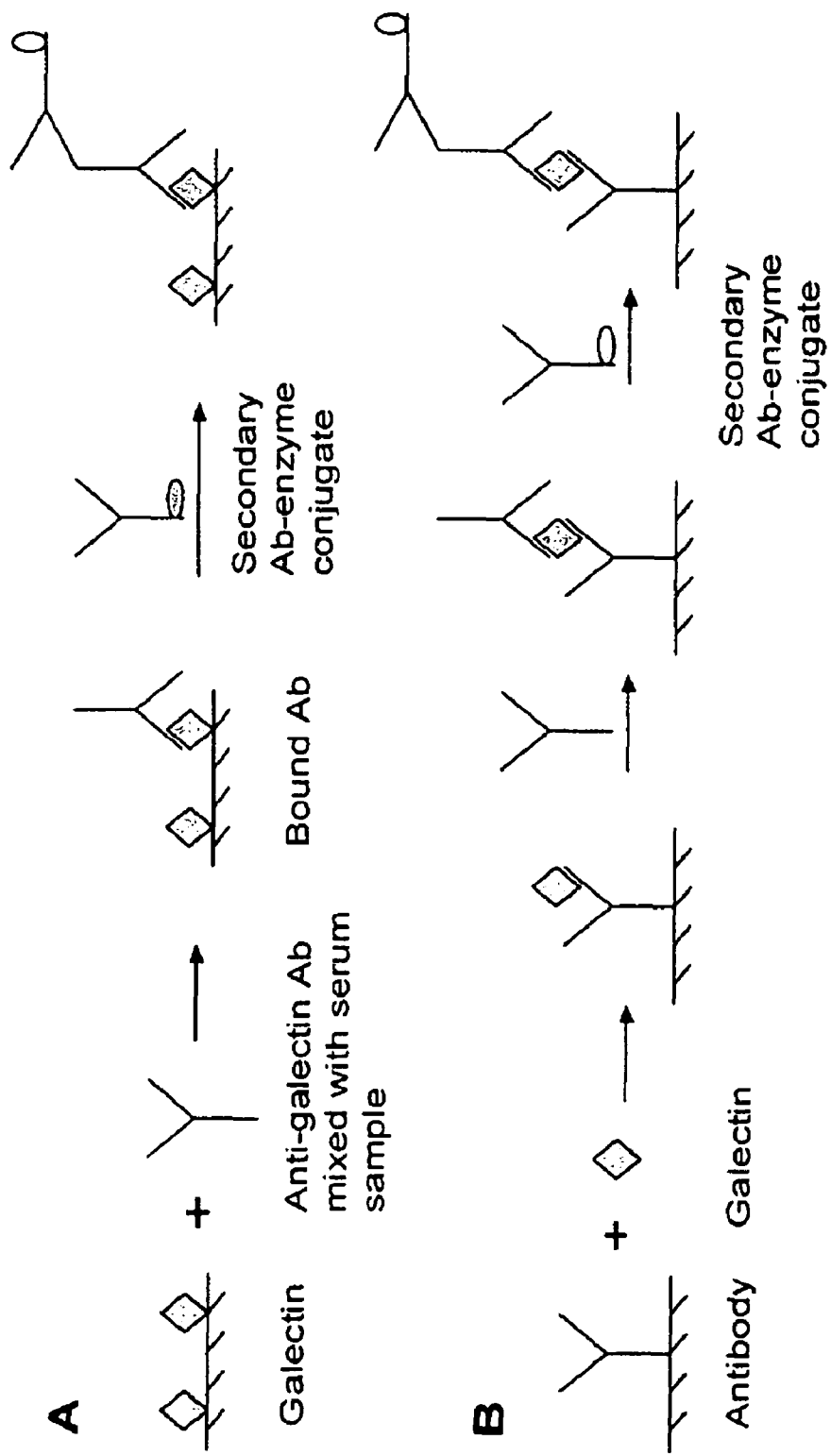
FIG. 9 is a schematic representation of immunoassay.

Solid phase immunoassays are used for quantitation of gal3, gal8a, and gal8g in biological samples. The presence of galectins in sera is examined by immunoassays as shown in FIG. 9A. In the immunoassay, the galectin is coated on a 96-well plate and the known amount of anti-galectin antibody (anti-gal3 or anti-gal8g) is pre-mixed with varying amount of standard antigen (galectin) or unknown sample (serum) and added to plate. The amount of galectin in the serum is measured from a standard curve. Alternatively, anti-galectin antibodies are coated and serum (or standard galectin) is added onto the wells, and the bound galectin is quantitated with the anti-galectin antibodies followed by secondary antibody conjugated to horseradish peroxidase as described elsewhere (Iurisci et al., 2000) and shown in FIG. 9B.

MS-PCR is performed to assess the methylation status of a particular group of CpG sites within a CpG island. The procedure entails initial modification of DNA by sodium bisulfite and subsequent amplification with primers specific for methylated (M primer) versus unmethylated (U primer) DNA (Herman et al., 1996). The difference between the CD-PCR described above and MS-PCR is the location of primer site. In CD-PCR, primers are designed from the regions outside the CpG islands and the methylation status of the CpG islands is investigated from cloning and sequencing of the PCR product. In MS-PCR, primers are chosen from the CpG sites to discriminate between methylated and unmethylated alleles following bisulfite treatment and thus the methylation status of the CpG islands is assessed directly from the PCR product. The PCR product is expected only in tubes where methylated DNA is mixed with the M primer and unmethylated DNA is mixed with U primer (see FIG. 10, illustrating exemplary sequences SEQ ID NO: 5 (methylated DNA modified by sodium bisulfite), SEQ ID NO: 6 (unmethylated DNA modified by sodium bisulfite), SEQ ID NO: 7 (U primer), and SEQ ID NO: 8 (M primer)). PCR amplification of modified or unmodified DNA with the primers specific for methylated or unmethylated DNA is achieved as described above.

Example 2 gal3 Promoter Methylation in Normal and Tumor Prostate Tissues gal3 promoter from stage I and II tumors is heavily methylated (most cytosines of 51 CpG sites), but from stage III tumors showed only few methylation sites, mostly between −199 to −252 nt (FIG. 12). The gal3 promoter from stage IV tumor was also lightly methylated between −112 to −227 nt. In normal prostate and BPH samples, the gal3 promoter was mostly unmethylated (FIG. 12).

Example 3

MS-PCR Assay for Detection of gal3 Promoter Methylation in Tissue, Serum and Urine Samples The methylated primers after taking into account the bisulfite conversion reaction were as follows: forward primer HuG3BPMF1, 5'-CGTTTCGTC-GGCGTTCG-3' (SEQ ID NO: 13) (ranging −9 to +8 of the promoter sequence, 20) and reverse primer HuG3BPMR1, 5'-CACGCAACTCAC-CGCTCG-3' (SEQ ID NO: 14) (ranging from +47 to +64 of the promoter sequence). To identify any unmethylated DNA allele, PCR was also performed using unmethylated primers. The PCR product obtained with the unmethylated primers serves also as a positive control for the presence of DNA in the PCR reaction, when MS-PCR with the methylated primers is negative. The unmethylated primers, designed by taking into account the bisulfite conversion reaction, were as follows: forward primer HuG3BPUF1, 5'-GAGGTTTGGAGTTAT-TGTTTTGTTGGTG-3' (SEQ ID NO: 15) (ranging −24 to +4 of the promoter sequence) and reverse primer HuG3BPUR1, 5'-CCCCACACAACTCACCACTCA-3' (SEQ ID NO: 16) (ranging from +47 to +67 of the promoter sequence). The PCR product is expected only in samples where methylated primers come in contact with the methylated DNA and unmethylated primers with the unmethylated DNA.

Figure 13:
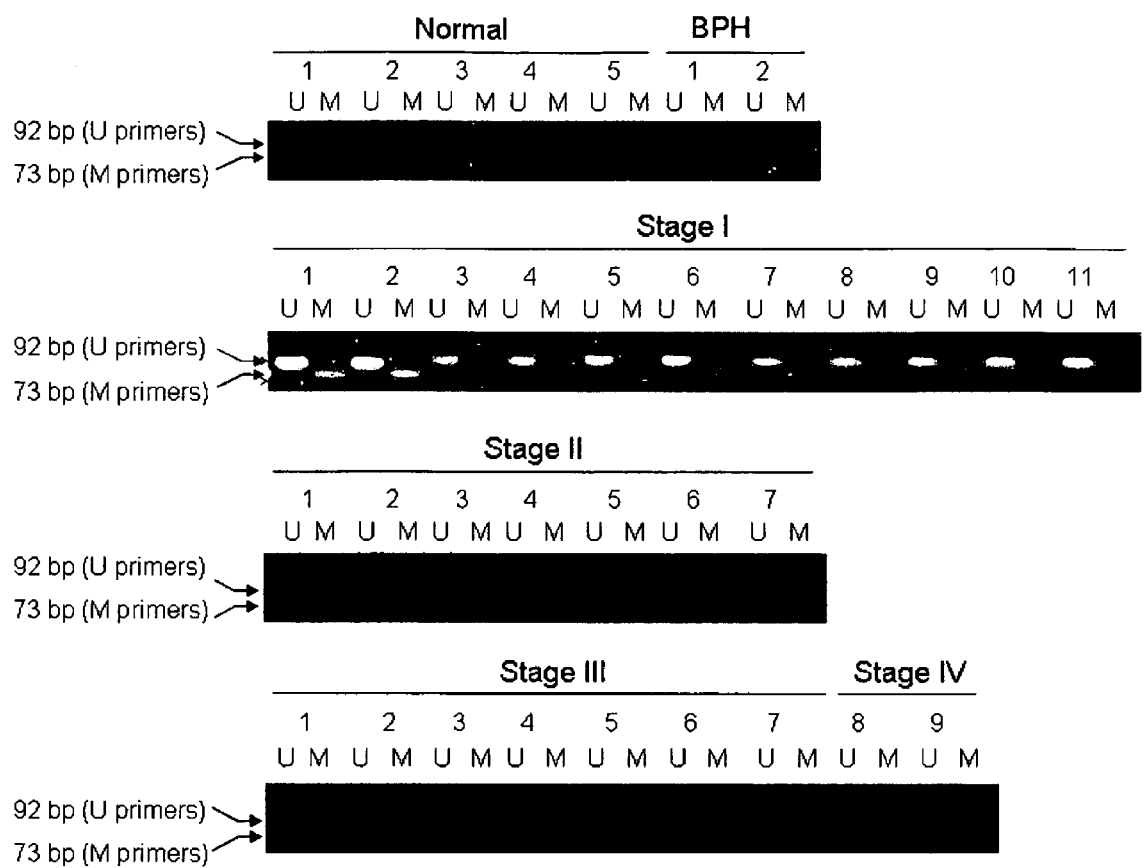
FIG. 13 shows PCR of bisulfite-treated DNA isolated from normal, BPH, and tumor prostate tissues with gal3 unmethylated (U) and methylated (M) primer pairs. The products 92 bp and 73 bp obtained from unmethylated and methylated primer pairs, respectively, are shown by arrows.

FIG. 13 and Table 2 show the results of gal3 PCR from 34 tissues (5 normal, 2 BPH, 11 stage I, 7 stage II, 7 stage III, and 2 stage IV) taken from tissue, serum and urine samples (see Table 2 for TNM classification, Gleason score, and source of the tissues including age and race), where an equal amount of bisulfite-treated DNA (75 ng) was used for each PCR reaction and the product was subjected to agarose gel electrophoresis on a 5% TopVision LE GQ agarose (Fermentas, Glen Burnie, Md.).

Example 4

MS-PCR Assay for Detection of gal3 Promoter Methylation in Urine Samples

Figure 14:
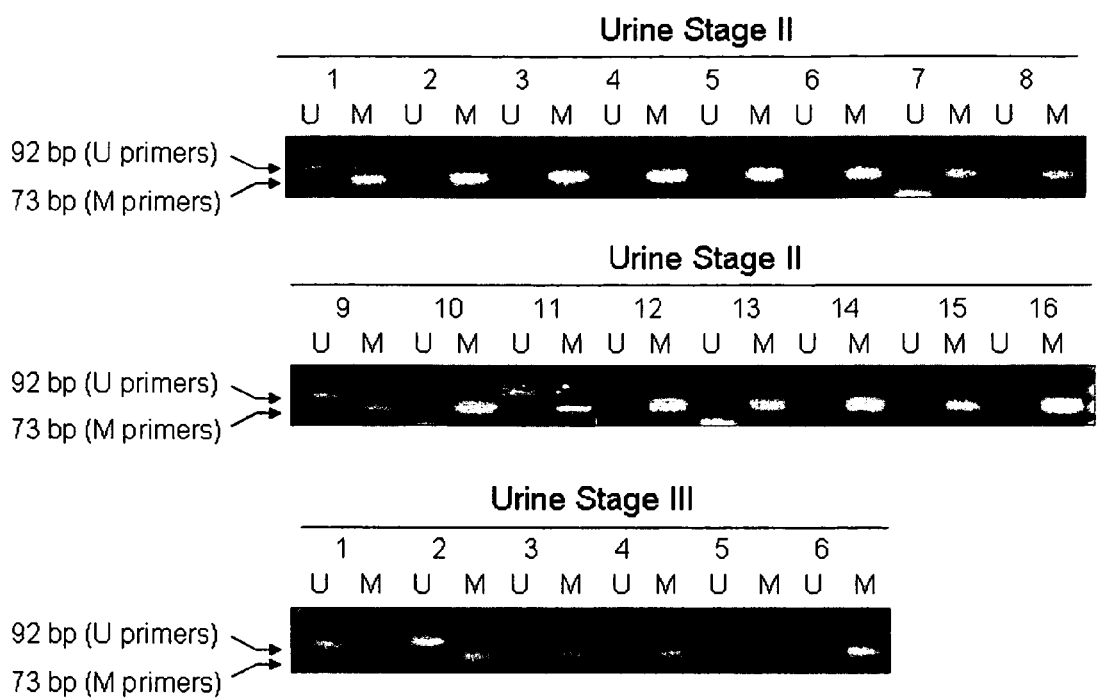
FIG. 14 shows PCR of bisulfite-treated DNA isolated from tumor urine samples with gal3 unmethylated (U) and methylated (M) primer pairs.

Urine samples were obtained from prostate cancer patients (tumor stage II and III) from the CHTN. DNA was isolated using Wizard Genomic DNA Purification kit (Promega, Madison, Wis.) and bisulfite-treated as previously described. Equal amount of bisulfite-treated DNA (75 ng) was used for each PCR reaction and the product was subjected to agarose gel electrophoresis on either 5% TopVision LE GQ agarose. gal3 MS-PCR was positive for all stage II urine specimens (16 of 16, very intense 73 bp product with the methylated primers, see FIG. 14). The assay was also positive for all stage III specimens (less intense band compared to stage II specimens) indicating the heterogeneous tumor content in the urine.

Analysis of additional specimens from normal individuals, patients with benign prostatic hyperplasia (BPH), bladder cancer patients without any prostate abnormality, and bladder cancer patients with prostate BPH, high-grade prostatic intraepithelial neoplasia (HGPIN) and kidney cancer was performed. DNA from urine was isolated using Wizard Genomic DNA Purification kit (Promega, Madison, Wis.) and bisulfite treated by EZ Gold Methylation kit (Zymo Research) as previously described. An equal amount of bisulfite treated DNA (75 ng) was used for each PCR reaction and the product was subjected to agarose gel electrophoresis on a 5% TopVision LE GQ agarose (Fermentas, Glen Burnie, Md.).

Figure 15:
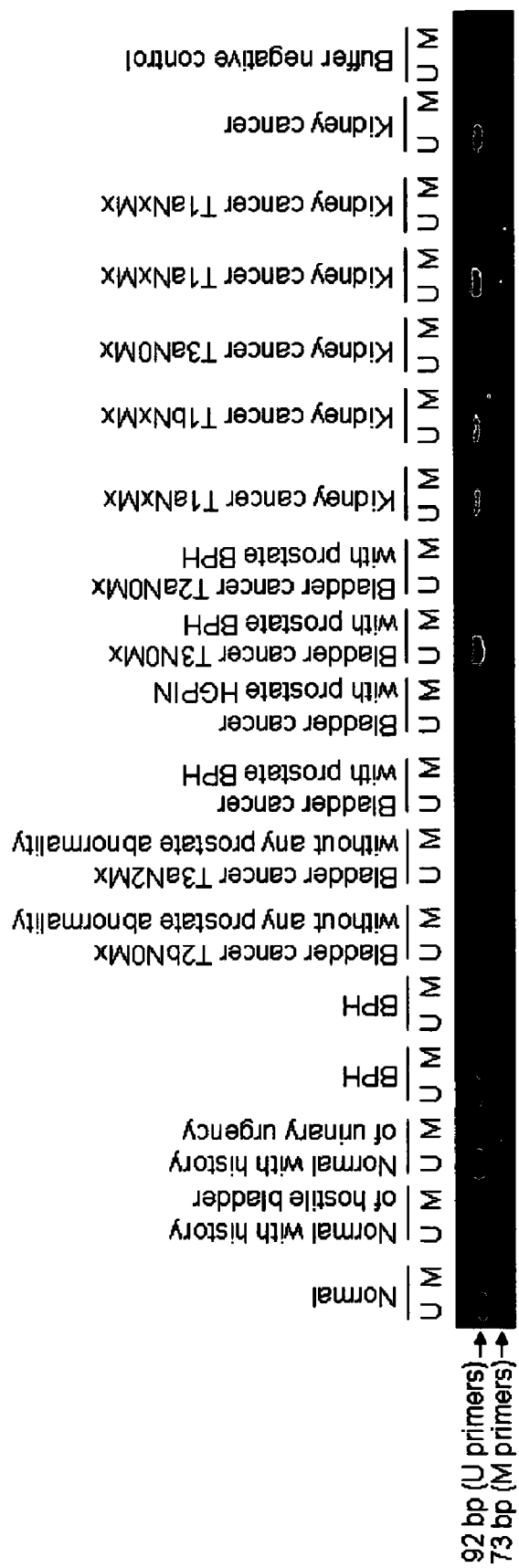
FIG. 15 shows PCR of bisulfite-treated DNA isolated from normal, BPH, and tumor prostate tissues with gal3 unmethylated (U) and methylated (M) primer pairs, as described in Example 4 below.

The MS-PCR results are set forth in FIG. 15. The products 92 bp and 73 bp obtained from unmethylated and methylated primer pairs, respectively, are shown by arrows. The results demonstrate that gal3 MS-PCR was generally negative for normal and BPH urine specimens except one (that from a bladder cancer patient with prostate BPH). The PCR was also negative for specimens from kidney cancer and bladder cancer patients without any prostate abnormality, indicating that the assay is specific to only prostate cancer. However, the gal3 MS-PCR was positive for the urine specimen from a bladder cancer patient with prostate HGPIN. HGPIN is believed to be a precursor lesion to the development of invasive prostatic adenocarcinoma. Thus, these results indicate that the MS-PCR assay constitutes a powerful tool to reliably identify not only early stages of prostate cancer, but also precursor lesion (HGPIN) in urine.

Example 5

MS-PCR Assay for Detection of GSTP1 Methylation

The gal3 MS-PCR assay is shown above to reliably identify all stage I and II prostate cancer tested. Negative results from this MS-PCR assay may indicate the test specimen is either normal or a tumor at a stage other than stage I and II.

A second assay was developed for detection of prostate cancers in Stage III or IV. This additional MS-PCR assay is based on the methylation pattern of the glutathione S-transferase P1 (GSTP1) gene to identify prostate cancer (stages III and above) (see FIG. 16). The unmethylated and methylated primers designed on a basis of results reported elsewhere (Singal et al., 2001), after taking into account the bisulfite conversion reaction were as follows: unmethylated forward primer GSTP1UF1, 5'-GGTTAGTTGTGTGGT-GATTTTGGG-3' (SEQ ID NO: 17) (ranging −196 to −173 nt of the promoter sequence), unmethylated reverse primer GSTP1UR1, 5'-AACCTCACAACCTC-CAAACC-3' (SEQ ID NO: 18) (from −26 to −7), methylated forward primer GSTP1MF1, 5'-TAGTTGCGCGGCGATTTC-3' (SEQ ID NO: 19) (from −193 to −176), and methylated reverse primer GSTP1MR1, 5'-AAAACCT-CGCGACCTCCG-3' (SEQ ID NO: 20) (from −22 to −5). Equal amount of bisulfite-treated DNA (75 ng) was used for each PCR reaction and the product was subjected to agarose gel electrophoresis on either 3% (panels 1-3) or 5% (panel 4) TopVision LE GQ agarose.

The results revealed that the GSTP1 MS-PCR detected all stage IV samples (2 out of 2), but only 3 samples of stage III out of 7 (FIG. 16). However, the GSTP1 MS-PCR was also positive for 9 out of 11 stage I and 6 out of 7 stage II samples. The GSTP1 MS-PCR was negative for BPH (2 out of 2) and normal samples, except 1 (out of 5) (FIG. 16).

The inability of GSTP1 MS-PCR to detect all tumor samples especially higher stage was probably due to the primer location, which was based on the promoter methylation results in the LNCaP cell line (Singal et al., 2001). The assay was performed again, using methylated primers (forward GSTP1MF2, 5'-CGGGGTGTAGCGGTCGTC-3' (SEQ ID NO: 21) ranging from −141 to −124 nt of the promoter sequence, and reverse primer GSTP1MR2, 5'-GCCCAATACTAAATCACGAC-3' (SEQ ID NO: 22) ranging from −74 to −53 nt) based on studies by Cairns et al., 2001, and tested them in stage III and IV prostate cancer samples. The corresponding unmethylated primers were as follows: forward GSTP1UF2, 5'-GATGTTTGGGGTGTAGTGGTTGTTG-3' (SEQ ID NO: 23) ranging from −147 to −123 nt and reverse GSTP1UR2, 5'-CCACCCCAATACTAAATCACAACACC-3' (SEQ ID NO: 24) ranging from −76 to −51 nt of the promoter sequence.

The sensitivity of the new MS-PCR with the GSTP1MF2 and GSTP1MR2 primer pairs was considerably higher (positive for 6 out of 7 samples; see the bottom panel of FIG. 16) as compared to the initial primer set.

Example 6

Figure 17:
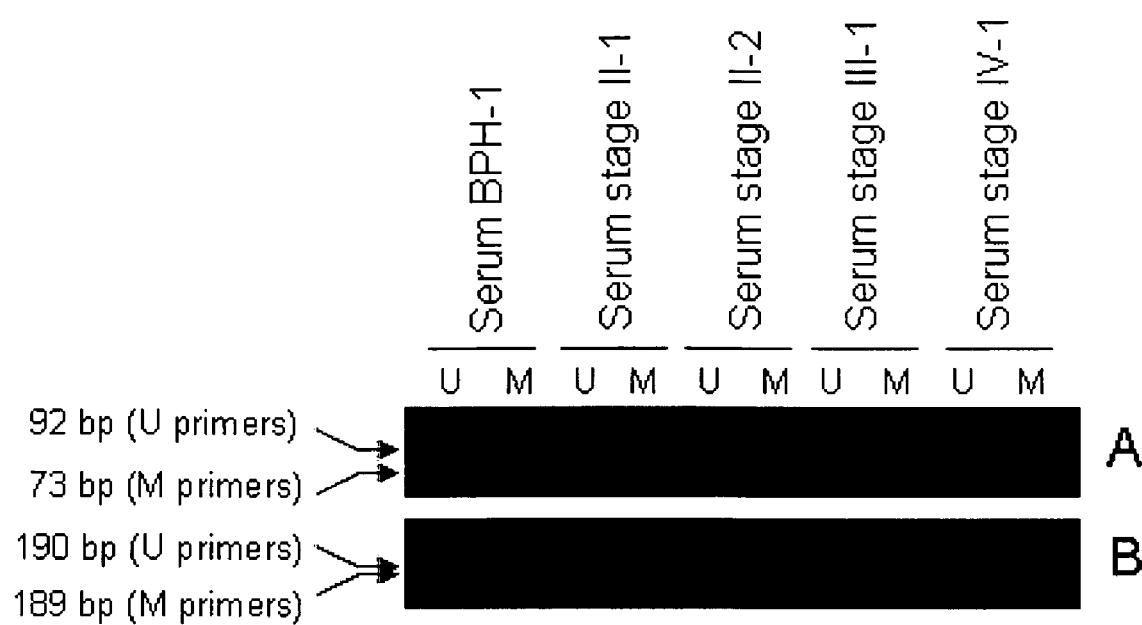
FIG. 17 shows PCR of bisulfite-treated DNA isolated from BPH and tumor serum samples with gal3 (A) and GSTP1 (B) unmethylated (U) and methylated (M) primer pairs.

Comparative Assessment of MS-PCR Assays for Detection of gal3 and GSTP1 Methylation in Urine and Serum Samples An MS-PCR assay similar to that of Example 5 was carried out on urine samples. Equal amount of bisulfite-treated DNA (75 ng) was used for each PCR reaction and the product was subjected to agarose gel electrophoresis on either 5% (A) or 3% (B) TopVision LE GQ agarose. Tumor specific sequences including GSTP1 were detected in DNA isolated from serum and urine (Goessl et al., 2000; Ziegler et al., 2002; Su et al. 2004; Hoque et al., 2005). Of the serum samples (obtained from Asterand, asterand.com; see also Table 2 for tumor type, age, and race) tested, gal3 MS-PCR was positive for stage II samples (2 out of 2), and as expected, negative for BPH (1 out of 1), stage III (1 out of 1), and stage IV (1 out of 1) samples (FIG. 17A). Further, the GSTP1 MS-PCR assay using the primer pair GSTP1MF1 and GSTP1MR1 identified all tumor serum samples (FIG. 17B).

Example 7

Combined Quantitative gal3 and GSTP1 MS-PCR Assays for Detection of Methylation in Urine and Serum Samples Gal3 MS-PCR assays are performed for the normal and tumor urine specimens using the methylated primers as described above. Should any sample of stage I or II fail to produce PCR product, methylation pattern of the gal3 promoter in these samples will be analyzed and the primers will be fine tuned.

For GSTP1 MS-PCR, several methylated primer pairs will be designed based on the previous studies (Hoque et al., *J. Clin. Oncol.*, 2005; 23:6569-6575; Singal et al., *Cancer Res.*, 2001; 61:4820-4826; Cairns et al., *Clin. Cancer Res.*, 2001; 7:2727-2730) and one pair will be chosen that works for all stages III and IV specimens. If necessary, cytosine methylation of the GSTP1 promoter will be analyzed in the tissue specimens in order to optimize the MS-PCR assay.

Urine samples will be initially tested with this GSTP1 assay to ensure detection of stage III and IV with nearly 100% specificity and 100% sensitivity. A quantitative PCR assay will be designed as previously described (Hoque et al., *Cancer Res.*, 2004; 64:5511-5517). Primer and probe design for GSTP1 will be based on the optimized GSTP1 MS-PCR assay.

The bisulfite-modified DNA will be used as a template for fluorescence-based real-time PCR (Taqman) as previously described (Hoque et al., *Cancer Res.*, 2004; 64:5511-5517). Primers and probes will be designed to specifically amplify the bisulfite-modified promoters of gal3 and GSTP1. Gene-specific probes will be obtained from Applied Biosystems (Foster City, Calif.), and primers will be obtained from Invitrogen Corporation (Carlsbad, Calif.). Each primer set (forward, reverse, and probe) will contain several CpG dinucleotides of the promoter sequence and numerous independent cytosine residues. The β-actin gene will be used as an internal reference. Leukocytes from a healthy individual will be methylated in vitro with excess SssI methyltransferase (New England Biolabs, Beverly, Mass.) to generate completely methylated DNA, which will be used in serial dilution for constructing calibration curves.

Methylation of gal3 and GSTP1 will be treated as a binary variable (methylation vs. no methylation) by dichotomizing each gene at zero. Proportions of methylated genes will be compared between tumor and control specimens using Fisher's exact test. For the purposes of this analysis, frequency of methylation positivity in tumor samples will be designated as "sensitivity". Sensitivity and specificity of the markers for disease will be calculated along with 95% confidence intervals using cross-tabulation, where sensitivity is defined as the number of true positive results divided by the number of true positive plus false negative results. Specificity is defined as the number of true negative results divided by the number of true negative plus false positive results.

The present Example should yield a quantitative non-invasive diagnostic platform consisting of the combined MS-PCR assays (gal3 and GSTP1) that reliably identifies early and advanced prostate cancer stages, including 100% of the stage I and II (the critical stage for effective treatment and cure) from urine.

Although the invention has been described with reference to the above examples, it will be understood that modifications and variations are encompassed within the spirit and scope of the invention. Accordingly, the invention is limited only by the following claims.

CITED REFERENCES

The contents of all cited references are incorporated herein by reference for all purposes.

Ahmed H, Allen H J, Sharma A, Matta K L. Human splenic galaptin: carbohydrate-binding specificity and characterization of the combining site. Biochemistry 1990; 29:5315-9.

Ahmed H, Sharma A, DiCioccio R A, Allen H J. Lymphoblastoid cell adhesion mediated by a dimeric and polymeric endogenous beta-galactoside-binding lectin (Galaptin) J Mol Recognition. 1992; 5:1-8.

Ahmed H, Fink N E, Vasta G R. A novel solid-phase assay for lectin binding: comparative studies on beta-galactoside-binding S-type lectins from fish, amphibian, and mammalian tissues. Ann N Y Acad. Sci. 1994a; 712:315-317.

Ahmed H, Fink N E, Vasta G R. Elasmobranch and teleost fish contain thiol-dependent β-galactoside binding lectins that cross-reactive with those identified and characterized in bovine spleen. Ann N Y Acad. Sci. 1994b; 712:318-20.

Ahmed H, Vasta G R. Galectins: conservation of functionally and structurally relevant amino acid residues defines two types of carbohydrate recognition domains. Glycobiology 1994; 4:545-9.

Ahmed H, Fink N E, Pohl J, Vasta G R. Galectin-1 from bovine spleen: Biochemical characterization, carbohydrate specificity and tissue-specific isoform profiles. J. Biochem (Tokyo). 1996a; 120:1007-19.

Ahmed H, Pohl J, Fink N E, Strobel F, Vasta G R. The primary structure and carbohydrate specificity of a β-galactosyl-binding lectin from toad (Bufo arenarum Hensel) ovary reveal closer similarities to the mammalian galectin-1 than to the galectin from the clawed frog *Xenopus laevis*. J Biol. Chem. 1996b; 271:33083-94.

Ahmed H, Bianchet M A, Amzel L M, Hirabayashi J, Kasai K, Giga-Hama Y, Tohda H, Vasta G R. Novel carbohydrate specificity of the 16 kDa galectin from *Caenorhabditis elegans*: Binding to blood group precursor oligosaccharides (type 1, type 2, $T_\alpha$, and $T_\beta$) and gangliosides. Glycobiology 2002; 12:451-61.

Ahmed H, Du S J, O'Leary N, Vasta, G R. Biochemical and molecular characterization of galectins from zebrafish (Danio rerio). Notochord-specific expression of a proto type galectin (Drgal 1-L2) during early embryogenesis. Glycobiology 2004; 14:219-32.

Ahmed, H., Banerjee, P. B., and Vasta, G. R. Differential expression of galectins in normal, benign and malignant prostate epithelial cells: Silencing of galectin-3 expression in prostate cancer by its promoter methylation. Biochem. Biophys. Res. Commun. 2007; 358: 241-6.

Akahani S, Nangia-Makker P, Inohara H, Kim H R, Raz A. Galectin-3: a novel antiapoptotic molecule with a functional BH1 (NWGR) domain of Bcl-2 family. Cancer Res. 1997; 57:5272-6.

Allen H J, Sharma A, Ahmed H, Piver M S, Gamarra M. Galaptin and galaptin-binding glycoconjugates in serum and effusions of carcinoma patients. Tumour Biol. 1993; 14:360-8.

Anker P, Lyautey J, Lederrey C, Stroun M. Circulating nucleic acids in plasma or serum. Clin Chim Acta. 2001; 313:143-6.

Avni O, Pur Z, Yefenof E, Baniyash M. Complement receptor 3 of macrophages is associated with galectin-1-like protein. J. Immunol. 1998; 160:6151-8.

Barondes S H, Cooper D N W, Gitt M A, Leffler H. Galectins. Structure and function of a large family of animal lectins. J Biol. Chem. 1994; 269:20807-10.

Benvenuto G, Carpentieri M L, Salvatore P, Cindolo L, Bruni C B, Chiariotti L Cell-specific transcriptional regulation and reactivation of galectin-1 gene expression are controlled by DNA methylation of the promoter region. Mol Cell Biol. 1996; 16:2736-43. Erratum in: Mol Cell Biol. 1996; 16:4590

Bianchet, M. A., Ahmed, H., Vasta, G. R., Amzel, L. M. A soluble β-galactosyl-binding lectin (galectin) from toad (Bufo arenarum Hensel) ovary: Crystallographic studies of two protein-sugar complexes. Proteins 2000; 40:378-88.

Bidon N, Brichory F, Hanash S, Bourguet P, Dazord L, Le Pennec J P. Two messenger RNAs and five isoforms for Po66-CBP, a galectin-8 homolog in a human lung carcinoma cell line. Gene. 2001 Aug. 22; 274:253-62.

Bidon-Wagner N, Le Pennec J P. Human galectin-8 isoforms and cancer. Glycoconj J. 2004; 19:557-63.

Botezatu I, Serdyuk O, Potapova G. et al. Genetic analysis of DNA excreted in urine: a new approach for detecting specific genomic DNA sequences from cells dying in an organism. Clin Chem. 2000; 46:1078-84.

Cairns P, Esteller M, Herman J G, Schoenberg M, Jeronimo C, Sanchez-Cespedes M, Chow N H, Grasso M, Wu L, Westra W B, Sidransky D. Molecular detection of prostate cancer in urine by GSTP1 hypermethylation. Clin Cancer Res. 2001; 7:2727-30.

Califice S, Castronovo V, Bracke M, van den Brule F. Dual activities of galectin-3 in human prostate cancer: tumor suppression of nuclear galectin-3 vs tumor promotion of cytoplasmic galectin-3. Oncogene. 2004; 23:7527-36.

Camby I, Belot N, Rorive S, Lefranc F, Maurage C A, Lahm H, Kaltner H, Hadari Y, Ruchoux M M, Brotchi J, Zick Y, Salmon I, Gabius H J, Kiss R. Galectins are differentially expressed in supratentorial pilocytic astrocytomas, astrocytomas, anaplastic astrocytomas and glioblastomas, and significantly modulate tumor astrocyte migration. Brain Pathol. 2001; 11:12-26.

Caplan A and Kratz A. Prostate-specific antigen and the early diagnosis of prostate cancer. Am J Clin Pathol 2002; 117: S104-8

Chiariotti L, Salvatore P, Benvenuto G, Bruni C B. Control of galectin gene expression. Biochimie. 1999; 81:381-8.

Cho M, Cummings R D. Galectin-1, a β-galactoside-binding lectin in Chinese hamster ovary cells. II. Localization and biosynthesis. J Biol. Chem. 1995; 270:5207-12.

Choufani G, Nagy N, Saussez S, Marchant H, Bisschop P, Burchert M, Danguy A, Louryan S, Salmon I, Gabius H J, Kiss R, and Hassid S. The levels of expression of galectin-1, galectin-3, and the Thomsen-Friedenreich antigen and their binding sites decrease as clinical aggressiveness increases in head and neck cancers, Cancer 1999; 86:2353-2363.

Colnot C, Ripoche M, Fowlis D, Cannon V, Scaerou F, Cooper D N W, Poirier F. The role of galectins in mouse development. Trends Glycosci Glycotechnol. 1997; 9:31-40.

Colnot C, Sidhu S S, Balmain N, Poirier F. Uncoupling of chondrocytes death and vascular invasion in mouse galectin 3 null mutant bones. Dev Biol. 2001; 229:203-14.

Cooper D N W. Galectinomics: a lesson in complexity. Biochim Biophys Acta 2002; 1572:209-31.

Cooper D N W, Barondes S H. Evidence for export of a muscle lectin from cytosol to extracellular matrix and for a novel secretory mechanism. J. Cell Biol. 1990; 110:1681-91.

Cooper D N W, Massa S M, Barondes S H. Endogenous muscle lectin inhibits myoblast adhesion to laminin. J. Cell Biol. 1991; 115:1437-48.

Costa M, Teixeira, V R, Junqueira M S, Costa F F, Camargo A A, Chammas R. Galectin-3 gene expression is silenced by methlyation of its promoter in murine melanoma cells. 1° Simpósio Avanços em Pesquisas Médicas dos Laboratórios de Investigaçqão Médica do HC-FMUSP, 2003, Sao Paulo, 2003; Abstract R256.

Danguy A, Rorive S, Decaestecker C, Bronckart Y, Kaltner H, Hadari Y R, Goren R, Zich Y, Petein M, Salmon I, Gabius H J, Kiss R. Immunohistochemical profile of galectin-8 expression in benign and malignant tumors of epithelial, mesenchymatous and adipous origins, and of the nervous system. Histol Histopathol. 2001; 16:861-8.

Ellerhorst J, Nguyen T, Cooper D N, Lotan D, Lotan R. Differential expression of endogenous galectin-1 and galectin-3 in human prostate cancer cell lines and effects of overexpressing galectin-1 on cell phenotype. Int J. Oncol. 1999a; 14:217-24.

Ellerhorst J, Troncoso P, Xu X C, Lee J, Lotan R. Galectin-1 and galectin-3 expression in human prostate tissue and prostate cancer. Urol Res. 1999b; 27:362-7.

Fackler M J, McVeigh M, Mehrotra J, Blum M A, Lange J, Lapides A, Garrett E, Argani P, Sukumar S. Quantitative multiplex methylation-specific PCR assay for the detection of promoter hypermethylation in multiple genes in breast cancer; Cancer Res., 64(13):4442-52 (2004).

Frommer M, McDonald L E, Millar D S, Collis C M, Watt F, Grigg G W, Molloy P L, Paul C L. A genomic sequencing protocol that yields a positive display of 5-methylcytosine residues in individual DNA strands. Proc Natl Acad Sci USA. 1992; 89:1827-31.

Gauthier L, Rossi B, Roux F, Termine E, Schiff C. Galectin-1 is a stromal cell ligand of the pre-B cell receptor (BCR) implicated in synapse formation between pre-B and stromal cells and in pre-BCR triggering. Proc Natl Acad Sci USA. 2002; 99:13014-9.

Gibson U E, Heid C A, Williams P M. A novel method for real time quantitative PCR. Genome Res. 1996; 6:986-94.

Glinsky V V, Glinsky G V, Rittenhouse-Olson K, Huflejt M E, Glinskii O V, Deutscher S L, Quinn T P. The role of Thomsen-Friedenreich antigen in adhesion of human breast and prostate cancer cells to the endothelium. Cancer Res. 2001; 61:4851-7.

Glinsky V V, Huflejt M E, Glinsky G V, Deutscher S L, Quinn T P. Effects of Thomsen-Friedenreich antigen-specific peptide P-30 on beta-galactoside-mediated homotypic aggregation and adhesion to the endothelium of MDA-MB-435 human breast carcinoma cells. Cancer Res. 2000; 60:2584-8.

Goessl C, Krause H, Muller M, Heicappell R, Schrader M, Sachsinger J, Miller K. Fluorescent methylation-specific polymerase chain reaction for DNA-based detection of prostate cancer in bodily fluids. Cancer Res. 2000; 60:5941-5.

Goletz S, Hanisch F G, Karsten U. Novel alphaGalNAc containing glycans on cytokeratins are recognized invitro by galectins with type II carbohydrate recognition domains. J Cell Sci. 1997; 110: 1585-96.

Gong H C, Honjo Y, Nangia-Makker P, Hogan V, Mazurak N, Bresalier R S, Raz A. The NH2 terminus of galectin-3 governs cellular compartmentalization and functions in cancer cells. Cancer Res. 1999; 59:6239-45.

Gotz W, Kasper M, Miosge N, Hughes R C. Detection and distribution of the carbohydrate binding protein galectin-3 in human notochord, invertebral disc and chordoma. Differentiation 1997; 62:149-57.

Gu M, Wang W, Song W K, Cooper D N, Kaufman S J. Selective modulation of the interaction of alpha 7 beta 1 integrin with fibronectin and laminin by L-14 lectin during skeletal muscle differentiation. J Cell Sci. 1994; 107:175-81.

Hadari Y R, Arbel-Goren R, Levy Y, Amsterdam A, Alon R, Zakut R, Zick Y. Galectin-8 binding to integrins inhibits cell adhesion and induces apoptosis. J Cell Sci. 2000; 113: 2385-97.

Hanahan D, Weinberg R A. The hallmarks of cancer. Cell 2000: 100:57-70.

Herman J G, Graff J R, Myohanen S, Nelkin B D, Baylin S B. Methylation-specific PCR: A novel PCR assay for methylation status of CpG islands. Proc Natl Acad Sci USA 1996; 93:9821-6.

Hernandez J D, Baum L G. Ah, sweet mystery of death! Galectins and control of fate. Glycobiology 2002; 12:127R-136R.

Hessels D, Verhaegh G W, Schalken J A, Witjes J A. Applicability of biomarkers in the early diagnosis of prostate cancer. Expert Rev Mol. Diagn. 2004; 4:513-26.

Hirabayashi J, Kasai K. The family of metazoan metal-independent β-galactoside-binding lectins:structure, function and molecular evolution. Glycobiology 1993; 3:297-304.

Hoque M O, Begum S, Topaloglu O, Jeronimo C, Mambo E, Westra W H, Califano J A, Sidransky D. Quantitative detection of promoter hypermethylation of multiple genes in the tumor, urine, and serum DNA of patients with renal cancer. Cancer Res. 2004; 64:5511-7.

Hoque M O, Topaloglu O, Begum S, Henrique R, Rosenbaum E, Van Criekinge W, Westra W H, Sidransky D. Quantitative methylation-specific polymerase chain reaction gene patterns in urine sediment distinguish prostate cancer patients from control subjects. J. Clin. Oncol. 2005; 23: 6569-75.

Hsu D K, Dowling C A, Jeng K C, Chen J T, Yang R Y, and Liu F T. Galectin-3 expression is induced in cirrhotic liver and hepatocellular carcinoma. Int. J. Cancer. 1999; 81:519-526.

Inohara H, Raz A. Functional evidence that cell surface galectin-3 mediates homotypic cell adhesion. Cancer Res. 1995; 55:3267-71.

Iurisci I, Tinari N, Natoli C, Angelucci D, Cianchetti E, Iacobelli S. Concentrations of galectin-3 in the sera of normal controls and cancer patients. Clin Cancer Res. 2000; 6:1389-93.

Jain S, Bhojwani A G, Mellon J K. Improving the utility of prostate specific antigen (PSA) in the diagnosis of prostate cancer: the use of PSA derivatives and novel markers. Postgrad Med J. 2002; 78:646-50

Jerónimo C, Henrique R, Hoque M O, Mambo E, Ribeiro F R, Varzim G, Oliveira J, Teixeira M R, Lopes C, Sidransky D. A quantitative promoter methylation profile of prostate cancer. Clin. Cancer Res. 2004; 10: 8472-8.

Jones P A, Baylin S B. The fundamental role of epigenetic events in cancer. Nat Rev Genet. 2002; 3:415-28.

Kadrofske M M, Openo K P, Wang J L. The human LGALS3 (galectin-3) gene: determination of the gene structure and functional characterization of the promoter. Arch Biochem Biophys. 1998; 349:7-20.

Keetch D W, Catalona W J, Smith D S. Serial prostatic biopsies in men with persistently elevated serum prostate specific antigen values. J. Urol. 1994; 151:1571-4.

Kondoh N, Hada A, Ryo A, Shuda M, Arai M, Matsubara O, Kimura F, Wakatsuki T, Yamamoto M. Activation of Galectin-1 gene in human hepatocellular carcinoma involves methylation-sensitive complex formations at the transcriptional upstream and downstream elements. Int J. Oncol. 2003; 23:1575-83.

Leffler H, Barondes S H. Specificity of binding of three soluble rat lung lectins to substituted and unsubstituted mammalian β-galactosides. J Biol. Chem. 1986; 261:10119-26.

Leffler H, Carlsson S, Hedlund M, Qian Y, Poirier F. Introduction to galectins. Glycoconj J. 2004; 19:433-40.

Leman E S, Cannon G W, Trock B J, Sokoll L J, Chan D W, Mangold L, Partin A W, Getzenberg R H. EPCA-2: A highly specific serum marker for prostate cancer. Urology 2007; 69:714-20.

Levy Y, Arbel-Goren R, Hadari Y R, Eshhar S, Ronen D, Elhanany E, Geiger B, Zick Y. Galectin-8 functions as a matricellular modulator of cell adhesion. J Biol. Chem. 2001; 276:31285-95.

Liao D I, Kapadia G, Ahmed H, Vasta G R, Herzberg O, Structure of S-lectin, a developmentally regulated vertebrate beta-galactoside binding protein. Proc Natl Acad Sci USA. 1994; 91:1428-32.

Liu F-T. Galectins: a new family of regulators of inflammation. Clin. Immunol. 2000; 97:79-88.

Liu F T, Rabinovich G A. Galectins as modulators of tumour progression. Nat Rev Cancer. 2005; 5:29-41.

Lotan R, Ito H, Yasui W, Yokozaki H, Lotan D, and Tahara E. Expression of a 31-kDa lactoside-binding lectin in normal human gastric mucosa and in primary and metastatic gastric carcinomas. Int. J. Cancer 1994; 56:474-480.

Matarrese P, Fusco O, Tinari N, Natoli C, Liu F T, Semeraro M L, Malorni W, Iacobelli S. Galectin-3 overexpression protects from apoptosis by improving cell adhesion properties. Int J. Cancer. 2000; 85:545-54.

Mizejewski, G. Role of integrins in cancer: Survey of expression patterns. Proc Soc Exp Biol Med. 1999; 222:124-38.

Nangia-Makker P, Conklin J, Hogan V, Raz A. Carbohydrate-binding proteins in cancer, and their ligands as therapeutic agents. Trends Mol. Med. 2002; 8:187-92.

Nangia-Makker P, Honjo Y, Sarvis R, Akahani S, Hogan V, Pienta K J, Raz A. Galectin-3 induces endothelial cell morphogenesis and angiogenesis. Am J. Pathol. 2000; 156:899-909.

Ozeki Y, Matsui T, Yamamoto Y, Funahashi M, Hamako J, Titani, K. Tissue fibronectin is an endogenous ligand for galectin-1. Glycobiology 1995; 5:255-61.

Pacis R A, Pilat M J, Pienta K J, Wojno K, Raz A, Hogan V, Cooper C R. Decreased galectin-3 expression in prostate cancer. Prostate. 2000; 44:118-23.

Park J W, Voss P G, Grabski S, Wang J L, Patterson R J. Association of galectin-1 and galectin-3 with Gemin4 in complexes containing the SMN protein. Nucleic Acids Res. 2001; 29:3595-602.

Paz A, Haklai R, Elad-Sfadia G, Ballan E, Kloog Y. Galectin-1 binds oncogenic H-Ras to mediate Ras membrane anchorage and cell transformation. Oncogene. 2001; 20:7486-93.

Perillo N L, Marcus M E, Baum L G. Galectins: versatile modulators of cell adhesion, cell proliferation, and cell death. J Mol. Med. 1998; 76:402-12.

Perillo N L, Pace K E, Seilhamer J J, Baum, L G. Apoptosis of T cells mediated by galectin-1. Nature 1995; 378:736-9.

Puche A C, Poirier F, Hair M, Barlett P F, Key B. Role of galectin-1 in the developing mouse olfactory system. Dev Biol. 1996; 179:274-87.

Rabinovich G A, Rubinstein N, Toscano M A. Role of galectins in inflammatory and immunomodulatory processes. Biochim Biophys Acta 2002; 1572:274-84.

Rabinovich G A, Toscano M A, Ilarregui J M, Rubinstein N. Shedding light on the immunomodulatory properties of galectins: novel regulators of innate and adaptive immune responses. Glycoconj J. 2004; 19:565-73.

Rosenberg I, Cherayil B J, Isselbacher K J, Pillai S. Mac-2-binding glycoproteins. Putative ligands for a cytosolic beta-galactoside lectin. J Biol. Chem. 1991; 266:18731-6.

Rubinstein N, Alvarez M, Zwirner N R, Toscano M A, Ilarregui J M, Bravo A, Mordoh J, Fainboim L, Podhajcer O L, Rabinovich G A. Targeted inhibition of galectin-1 gene expression in tumor cells results in heightened T cell-mediated rejection; A potential mechanism of tumor-immune privilege. Cancer Cell. 2004; 5:241-51.

Salvatore P, Benvenuto G, Caporaso M, Bruni C B, Chiariotti L. High resolution methylation analysis of the galectin-1 gene promoter region in expressing and nonexpressing tissues. FEBS Lett. 1998; 421:152-8.

Schwarz F P, Ahmed H, Bianchet M A, Amzel L M, Vasta G R. Thermodynamics of bovine spleen galectin-1 binding to disaccharides: correlation with structure and its effect on oligomerization at the denaturation temperature. Biochemistry. 1998; 37:5867-77.

Schwarz Jr G, Remmelink M, Decaestecker C, Gielen I, Budel V, Burchert M, Darro F, Danguy A, Gabius H J, Salmon I, and Kiss R. Galectin fingerprinting in tumor diagnosis. Differential expression of galectin-3 and galectin-3 binding sites, but not galectin-1, in benign vs malignant uterine smooth muscle tumors, Am. J. Clin. Pathol. 1999; 111:623-631.

Singal R, van Wert J, Bashambu M. Cytosine methylation represses glutathione S-transferase P1 (GSTP1) gene expression in human prostate cancer cells. Cancer Res. 2001; 61:4820-6.

Stewart D A, Cooper C R, Sikes R A. Changes in extracellular matrix (ECM) and ECM-associated proteins in the metastatic progression of prostate cancer. Reprod Biol Endocrinol. 2004; 2:2-14.

Su Z Z, Lin J, Shen R, Fisher P E, Goldstein N I, Fisher P B. Surface-epitope masking and expression cloning identifies the human prostate carcinoma tumor antigen gene PCTA-1a member of the galectin gene family. Proc Natl Acad Sci USA. 1996; 93:7252-7.

Su Y H, Wang M, Brenner D E. et al. Human urine contains small, 150 to 250 nucleotide-sized, soluble DNA derived from the circulation and may be useful in the detection of colorectal cancer. J Mol. Diagn. 2004; 6:101-7.

Symons A, Cooper D N, Barclay A N. Characterization of the interaction between galectin-1 and lymphocyte glycoproteins CD45 and Thy-1. Glycobiology. 2000; 10:559-63.

Thompson I M, Pauler D K, Goodman P J, Tangen C M, Lucia M S, Parnes H L, Minasian L M, Ford L G, Lippman S M, Crawford E D, Crowley J J, Coltman C A Jr. Prevalence of prostate cancer among men with a prostate-specific antigen level=4.0 ng per milliliter. New Eng J. Med. 2004; 350:2239-46.

Tokumaru Y, Harden S V, Sun D I, Yamashita K, Epstein J I, Sidransky D. Optimal use of a panel of methylation markers with GSTP1 hypermethylation in the diagnosis of prostate adenocarcinoma. Clin Cancer Res. 2004; 10:5518-22.

van den Brule F, Califice S, Castronovo V. Expression of galectins in cancer: a critical review. Glycoconj J. 2004; 19:537-42.

van der Brule F A, Waltregny D, Castronovo V. Increased expression of galectin-1 in carcinoma-associated stroma predicts poor outcome in prostate carcinoma patients. J. Pathol. 2001; 193:80-7.

Vasta G R, Ahmed H, Amzel L M, Bianchet M A. Amphibian galectins: molecular structure, properties and evolution Trends Glycosci Glycotechnol. 1997; 9:131-44.

Vasta G R, Quesenberry M, Ahmed H, O'Leary N. C-type Lectins and Galectins Mediate Innate and Adaptive Immune Functions: Their Roles in the Complement Activation Pathway. Develop Comp Immunol. 1999; 23:401-20.

Vasta G R., Ahmed H, Du S-J, Henrikson, D. Galectins in teleost fish: Zebrafish (Danio rerio) as a model species to address their biological roles in development and innate immunity. Glycoconjugate J, 2004a; 21:503-21.

Vasta G R, Ahmed H, Odom E W. Structural and Functional Diversity of Lectin Repertoires in Invertebrates, Protochordates, and Ectothermic Vertebrates. Current Opinion Struct Biol. 2004b; 14:617-30.

Vener T, Derecho C, Baden J, Wang H, Rajpurohit Y, Skelton J, Mehrotra J, Varde S, Chowdary D, Stallings W, Leibovich B, Robin H, Pelzer A, Schafer G, Auprich M, Mannweiler S, Amersdorfer P, Mazumder A. Development of a multiplexed urine assay for prostate cancer diagnosis. Clin Chem. 2008; 54:874-82.

Warfield P R, Makker P N, Raz A, Ochieng J. Adhesion of human breast carcinoma to extracellular matrix proteins is modulated by galectin-3. Invasion Metastasis. 1997; 17(2): 101-12.

Warnecke P M, Bestor T H. Cytosine methylation and human cancer. Curr Opin Oncol. 2000; 12:68-73.

Xu X C, el-Naggar A K, and Lotan R. Differential expression of galectin-1 and galectin-3 in thyroid tumors. Potential diagnostic implications. Am. J. Pathol. 1995; 147:815-822.

Yang R—Y, Hsu D K, Liu F-T. Expression of galectin-3 modulates T cell growth and apoptosis. Proc Natl Acad Sci USA. 1996; 93:6737-42.

Yang R Y, Hsu D K, Yu L, Ni J, Liu F T. Cell cycle regulation by galectin-12, a new member of the galectin superfamily. J Biol. Chem. 2001; 276:20252-60.

Yu F, Finley R L Jr, Raz A, Kim H R. Galectin-3 translocates to the perinuclear membranes and inhibits cytochrome c release from the mitochondria. A role for synexin in galectin-3 translocation. J Biol. Chem. 2002; 277:15819-27.

Zhou Q, Cummings R D. L-14 lectin recognition of laminin and its promotion of in vitro cell adhesion. Arch Biochem Biophys. 1993; 300:6-17.

Zick Y, Eisenstein M, Goren R A, Hadari Y R, Levy Y, Ronen D. Role of galectin-8 as a modulator of cell adhesion and cell growth. Glycoconj J. 2004; 19:517-26.

Ziegler A, Zangemeister-Wittke U, Stahel R A. Circulating DNA: a new diagnostic gold mine? Cancer Treat Rev. 2002; 28:255-71.

TABLE 1

Summary of current status and expected results of galectin expression and their promoter methylation in BPH, PIN, and various stages of PC

|  | gal3 | | gal8g | |
|---|---|---|---|---|
|  | mRNA/ protein | Promoter methylation | mRNA/ protein | Promoter methylation |
| BPH | = | = | = | = |
| PIN | = | = | NP | NP |
| Stage I | << | >> | > | < |
| Stage II | << | >> | >> | << |
| Stage III | < | > | > | < |
| Stage IV (Metastatic) | < | > | NP | NP |

=, almost equal to normal prostate tissue;
>, greater than normal;
<, less than normal;
NP, not predictable

TABLE 2

Summary of MS-PCR results from tissue (T), serum (S) and urine (U) DNA

| Sample T/S/U | Tissue type | AJCC Stage | AJCC TNM classific | Gleason score | Age | Race | Tumor content | Specimen source | Specimen ID | gal3 methyl-lation | gal3 MS-PCR | GSTP1 MS-PCR |
|---|---|---|---|---|---|---|---|---|---|---|---|---|
| N-1 (T) | Normal | NA | NA | NA | 66 | Caucasian | NA | Ambion | 0505-006 | Negl | − | − |
| N-2 (T) | Normal | NA | NA | NA | 79 | Caucasian | NA | Ambiom | 0505-007-1 | Negl | − | − |
| N-3 (T) | Normal | NA | NA | NA | 66 | Caucasian | NA | Ambion | 0505-007-2 | Negl | − | − |
| N-4 (T) | Normal | NA | NA | NA | 59 | Caucasian | NA | NDRI | OD23155 | ND | − | − |
| N-5 (T) | Normal | NA | NA | NA | 73 | U | NA | NDRI | OD23791 | ND | − | + |
| B-1 (T) | BPH | NA | NA | NA | 78 | U | NA | NDRI | 83-1107 | Negl | − | − |
| B-2 (T) | BPH | NA | NA | NA | U | U | NA | NDRI | 0056582-01 | Negl | − | − |
| I-1 (T) | Tumor | I | T1aNxMx | U | 60 | U | U | Collaborat | 244850 | ND | + | − |
| I-2 (T) | Tumor | I | T1aNxMx | 3 + 3 = 6 | 81 | U | U | Collaborat | 239521 | ND | + | − |
| I-3 (T) | Tumor | I | T1aNxMx | 3 + 3 = 6 | 74 | U | U | Collaborat | 238708 | ND | + | + |
| I-4 (T) | Tumor | I | T1aNxMx | 3 + 3 = 6 | 76 | U | U | Collaborat | 233011 | ND | + | + |
| I-5 (T) | Tumor | I | T1aNxMx | 2 + 3 = 5 | 85 | U | U | Collaborat | 218496 | ND | + | + |
| I-6 (T) | Tumor | I | T1aNxMx | 4 + 3 = 7 | 78 | U | U | Collaborat | 218163 | High | + | + |
| I-7 (T) | Tumor | I | T1aNxMx | 3 + 3 = 6 | 67 | U | U | Collaborat | 211841 | ND | + | + |
| I-8 (T) | Tumor | I | T1aNxMx | 4 + 5 = 9 | 66 | U | U | Collaborat | 209668 | ND | + | + |
| I-9 (T) | Tumor | I | T1aNxMx | 3 + 2 = 5 | 77 | U | U | Collaborat | 209667 | ND | + | + |
| I-10 (T) | Tumor | I | T1aNxMx | 3 + 4 = 7 | 64 | U | U | Collaborat | 207087 | ND | + | + |
| I-11 (T) | Tumor | I | T1aNxMx | 3 + 4 = 7 | 70 | U | U | Collaborat | 204782 | ND | + | + |
| II-1 (T) | Tumor | II | T2cNxMx | 3 + 4 = 7 | 63 | African | 15% | Ambion | 0505-023 | High | + | + |
| II-2 (T) | Tumor | II | T2cNxMx | 3 + 4 = 7 | 69 | Caucasian | 20% | CHTN | MAD06-00234 | High | + | + |
| II-3 (T) | Tumor | II | T2cNxMx | 3 + 3 = 6 | 48 | Caucasian | 15% | CHTN | MAD06-00550 | High | + | + |
| II-4 (T) | Tumor | II | T2cNxMx | 3 + 4 = 7 | 61 | Caucasian | 10% | CHTN | MAD07-00014 | High | + | + |
| II-5 (T) | Tumor | II | T2NxMx | 3 + 4 = 7 | 73 | U | 2.6% | NDRI | OD23791 | High | + | − |
| II-6 (T) | Tumor | II | T2cNxMx | 3 + 3 = 6 | 63 | Caucasian | 10% | CHTN | MAD06-00581 | High | + | + |
| II-7 (T) | Tumor | II | T2cNxMx | 3 + 3 = 6 | 50 | African | U | CHTN | MAD06-00504 | High | + | + |
| III-1 (T) | Tumor | III | T3N0MX | 3 + 4 = 7 | 62 | Caucasian | U | Ambion | 0405-037 | Low | − | + |
| III-2 (T) | Tumor | III | T3bN0Mx | 4 + 3 = 7 | 48 | Caucasian | 90% | CHTN | MAD03-01617 | High | + | + |
| III-3 (T) | Tumor | III | T3aNxMx | 3 + 3 = 6 | 58 | Caucasian | 20% | CHTN | MAD05-00155 | Low | − | + |
| III-4 (T) | Tumor | III | T3aNxMx | 4 + 3 = 7 | 66 | Caucasian | 10% | CHTN | MAD06-00118 | ND | − | + |
| III-5 (T) | Tumor | III | T3aNxMx | 4 + 3 = 7 | 66 | Caucasian | 25% | CHTN | MAD06-00536 | Low | − | + |
| III-6 (T) | Tumor | III | T3aNxMx | 3 + 3 = 6 | 44 | Caucasian | 30% | CHTN | MAD06-00681 | Low | − | + |
| III-7 (T) | Tumor | III | T3NxMx | 4 + 3 = 7 | 45 | U | U | NDRI | OD20866 | Low | − | − |
| IV-1 (T) | Tumor | IV | T3bN1Mx | 5 + 5 = 10 | 59 | Caucasian | 80% | NDRI | OD23155 | Low | − | + |
| IV-2 (T) | Tumor | IV | T3bN1Mx | U | 66 | U | U | CHTN | MAD05-00059 | Low | − | + |
| B-1 (S) | BPH | NA | NA | NA | U | U | NA | NDRI | 0056582-02 | ND | − | − |
| II-1 (S) | Tumor | II | T2bN0Mx | 4 + 3 = 7 | 63 | Caucasian | U | Asterand | 55916A2 | ND | + | + |
| II-2 (S) | Tumor | II | T2cN0Mx | 3 + 3 = 6 | U | Caucasian | U | Asterand | 47256A1 | ND | + | + |
| III-1 (S) | Tumor | III | T3aN0Mx | 3 + 4 = 7 | 66 | Caucasian | U | Asterand | 42629A1 | ND | − | + |
| IV-1 (S) | Tumor | IV | T3aN1Mx | 4 + 4 = 8 | 59 | Caucasian | U | Asterand | 53962A1 | ND | − | + |
| II-1 (U) | Tumor | II | T2cNxMx | 3 + 4 = 7 | 56 | Caucasian | 40% | CHTN | TPF12611 | ND | + | ND |
| II-2 (U) | Tumor | II | T2cNxMx | 3 + 4 = 7 | 71 | African | 40% | CHTN | TPF12760 | ND | + | ND |

TABLE 2-continued

Summary of MS-PCR results from tissue (T), serum (S) and urine (U) DNA

| Sample T/S/U | Tissue type | AJCC Stage | AJCC TNM classific | Gleason score | Age | Race | Tumor content | Specimen source | Specimen ID | gal3 methyl-lation | gal3 MS-PCR | GSTP1 MS-PCR |
|---|---|---|---|---|---|---|---|---|---|---|---|---|
| II-3 (U) | Tumor | II | T2aNxMx | 3 + 3 = 6 | 58 | Caucasian | 5% | CHTN | TPF12646 | ND | + | ND |
| II-4 (U) | Tumor | II | T2cNxMx | 3 + 4 = 7 | 61 | Caucasian | 15% | CHTN | TPF12671 | ND | + | ND |
| II-5 (U) | Tumor | II | T2cNxMx | 3 + 4 = 7 | 68 | Caucasian | 10% | CHTN | TPF12796 | ND | + | ND |
| II-6 (U) | Tumor | II | T2aNxMx | 1 + 1 = 2 | 70 | Caucasian | <1% | CHTN | TPF12624 | ND | + | ND |
| II-7 (U) | Tumor | II | T2cNxMx | 3 + 4 = 7 | 62 | Caucasian | 5% | CHTN | TPF12934 | ND | + | ND |
| II-8 (U) | Tumor | II | T2cNxMx | 3 + 3 = 6 | 69 | Caucasian | 10% | CHTN | TPF12827 | ND | + | ND |
| II-9 (U) | Tumor | II | T2cNxMx | 3 + 3 = 6 | 64 | Caucasian | <5% | CHTN | TPF12714 | ND | + | ND |
| II-10 (U) | Tumor | II | T2cN0Mx | 3 + 4 = 7 | 65 | Caucasian | 60% | CHTN | TPF12628 | ND | + | ND |
| II-11 (U) | Tumor | II | T2cNxMx | 3 + 3 = 6 | 52 | Caucasian | 5% | CHTN | TPF12890 | ND | + | ND |
| II-12 (U) | Tumor | II | T2cN0Mx | 4 + 4 = 8 | 63 | Caucasian | 10% | CHTN | TPF12876 | ND | + | ND |
| II-13 (U) | Tumor | II | T2cNxMx | 3 + 3 = 6 | 47 | Caucasian | 10% | CHTN | TPF12798 | ND | + | ND |
| II-14 (U) | Tumor | II | T2cNxMx | 3 + 3 = 6 | 67 | Caucasian | 5% | CHTN | TPF12701 | ND | + | ND |
| II-15 (U) | Tumor | II | T2aNxMx | 3 + 3 = 6 | 54 | Caucasian | 5% | CHTN | TPF12664 | ND | + | ND |
| II-16 (U) | Tumor | II | T2bN0Mx | 4 + 3 = 7 | 70 | Caucasian | 15% | CHTN | TPF12857 | ND | + | ND |
| III-1 (U) | Tumor | III | T3aNxMx | 4 + 3 = 7 | 59 | Caucasian | 10% | CHTN | TPF12717 | ND | + | ND |
| III-2 (U) | Tumor | III | T3aNxMx | 4 + 5 = 9 | 63 | Caucasian | 20% | CHTN | TPF12936 | ND | + | ND |
| III-3 (U) | Tumor | III | T3aNxMx | 3 + 3 = 6 | 54 | Caucasian | <5% | CHTN | TPF12738 | ND | + | ND |
| III-4 (U) | Tumor | III | T3aNxMx | 3 + 4 = 7 | 51 | Caucasian | 40% | CHTN | TPF12941 | ND | + | ND |
| III-5 (U) | Tumor | III | T3aN0Mx | 4 + 3 = 7 | 62 | Caucasian | 20% | CHTN | TPF12782 | ND | + | ND |
| III-6 (U) | Tumor | III | T3aNxMx | 4 + 4 = 8 | 57 | Caucasian | 30% | CHTN | TPF12846 | ND | + | ND |

NA, not applicable; U, unknown; Negl, negligible; ND, not determined
AJCC TNM Definitions:
Primary tumor (T):
TX: Primary tumor cannot be assessed
T0: No evidence of primary tumor
T1: Clinically inapparent tumor not palpable nor visible by imaging (T1a, Tumor incidental histologic finding in 5% or less; T1b, Tumor incidental histologic finding in more than 5%; T1c: Tumor identified by needle biopsy (e.g., because of elevated PSA)
T2: Tumor confined within prostate (T2a, Tumor involves 50% or less of one lobe; T2b, Tumor involves more than 50% of one lobe but not both lobes; T2c, Tumor involves both lobes)
T3: Tumor extends through prostate capsule (T3a, Extracapsular extension (unilateral or bilateral); T3b, Tumor invades seminal vesicle(s))
T4: Tumor is fixed or invades adjacent structures other than seminal vesicles: bladder neck, external sphincter, rectum, levator muscles, or pelvic wall
Regional lymph nodes (N):
NX: Lymph nodes were not assessed;
N0: No regional lymph node metastasis;
N1: Metastasis in regional lymph node(s)
Distant metastasis (M):
MX: Distant metastasis cannot be assessed;
M0: No distant metastasis;
M1: Distant metastasis (M1a, Nonregional lymph node; M1b, Bone; M1c, Other site +/− bone)

What is claimed is:

1. A method for determining the presence of prostate cancer in a subject, the method comprising:
    obtaining a biological sample from the subject;
    determining the level of gal3 promoter methylation; and
    comparing the level of gal3 promoter methylation in the sample from the subject relative to the level of gal3 promoter methylation found in a normal biological sample of the same type, wherein an increase in the level of gal3 promoter methylation in the sample from the subject relative to the level in the normal biological sample is indicative of the presence of prostate cancer in the subject and a relative level of increased methylation in the sample from the subject relative to the level in the normal biological sample is indicative of the stage of the cancer and wherein the biological sample is selected from prostate tissue, urine and serum.

2. The method of claim 1, wherein the increased gal3 promoter methylation is indicative of early stage prostate cancer, wherein the cancer is Stage I or Stage II prostate cancer.

3. The method of claim 1, wherein the increased gal3 promoter methylation is indicative of late stage prostate cancer, wherein the cancer is Stage III or Stage IV prostate cancer.

4. The method of claim 1, wherein the high relative level of increased methylation is high.

5. The method of claim 4, wherein the high relative level of increased gal3promoter methylation is indicative of early stage prostate cancer, wherein the cancer is Stage I or Stage II prostate cancer.

6. The method of claim 1, wherein the relative level of increased methylation is low.

7. The method of claim 6, wherein the low relative level of increased gal3 promoter methylation is indicative of late stage prostate cancer, wherein the cancer is Stage III or Stage IV prostate cancer.

8. The method of claim 1, wherein the level of gal3 promoter methylation is determined by PCR.

9. An assay for determining the presence of prostate cancer in a subject, the assay comprising:
    isolating a single-stranded DNA encoding gal3 from a biological sample taken from the subject, wherein the biological sample is selected from prostate tissue, urine and serum;
    treating the single-stranded DNA with bisulfite to convert non-methylated cytosine into uracil; and
    determining the level of methylation of the gal3 promoter region of the single stranded DNA, wherein the presence of gal3 promoter methylation is an indication of the presence of prostate cancer in the subject.

10. The assay of claim 9, wherein the prostate cancer is any of HGPIN, Stage I prostate cancer, Stage II prostate cancer, Stage III prostate cancer or Stage IV prostate cancer.

* * * * *